US012810476B2

(12) United States Patent
Ding et al.

(10) Patent No.: US 12,810,476 B2
(45) Date of Patent: Nov. 24, 2026

(54) METHOD AND SYSTEM FOR MEDICAL IMAGING

(71) Applicant: SHANGHAI UNITED IMAGING HEALTHCARE CO., LTD., Shanghai (CN)

(72) Inventors: Shihui Ding, Shanghai (CN); Biao Sun, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 434 days.

(21) Appl. No.: 18/460,501

(22) Filed: Sep. 1, 2023

(65) Prior Publication Data

US 2024/0087168 A1 Mar. 14, 2024

(30) Foreign Application Priority Data

Sep. 1, 2022 (CN) ........................ 202211069678.6
Sep. 21, 2022 (CN) ........................ 202211152194.8
Dec. 14, 2022 (CN) ........................ 202211608477.9

(51) Int. Cl.
*A61B 6/00* (2024.01)
*G06T 7/00* (2017.01)
(Continued)

(52) U.S. Cl.
CPC ................ *G06T 7/97* (2017.01); *A61B 6/545* (2013.01); *A61B 6/547* (2013.01); *G06T 7/73* (2017.01);
(Continued)

(58) Field of Classification Search
CPC .... G06T 7/97; G06T 7/73; G06T 7/80; G06T 2207/10081; G06T 2207/20081;
(Continued)

(56) References Cited

U.S. PATENT DOCUMENTS

2006/0203131 A1 9/2006 Gunji
2008/0064953 A1* 3/2008 Falco .................. A61N 5/1049 600/427
2012/0163536 A1 6/2012 Neethimanickam et al.
2013/0058545 A1 3/2013 Pearson, Jr. et al.
(Continued)

FOREIGN PATENT DOCUMENTS

CN 204698582 U 10/2015
CN 107669284 A 2/2018
(Continued)

OTHER PUBLICATIONS

First Office Action in Chinese Application No. 202211152194.8 mailed on Jul. 1, 2025, 10 pages.

*Primary Examiner* — Uzma Alam
*Assistant Examiner* — Mamadou Faye
(74) *Attorney, Agent, or Firm* — METIS IP LLC

(57) ABSTRACT

A method for medical imaging is provided. The method may include obtaining historical state information of a scanning region in a historical scan and current state information of the scanning region in a current scan to be performed; determining whether historical parameter values of one or more imaging parameters used in the historical scan need to be updated based on a comparison result between the historical state information and the current state information; in response to determining that the historical parameter values of the one or more imaging parameters used in the historical scan need to be updated, determining updated parameter values of the one or more imaging parameters based on the historical state information and the current state information; and directing a medical imaging device to perform the current scan based on the updated parameter values of the one or more imaging parameters.

19 Claims, 13 Drawing Sheets

(51) Int. Cl.
*G06T 7/73* (2017.01)
*G06T 7/80* (2017.01)

(52) U.S. Cl.
CPC ...... *G06T 7/80* (2017.01); *G06T 2207/10081* (2013.01); *G06T 2207/20081* (2013.01); *G06T 2207/30244* (2013.01)

(58) Field of Classification Search
CPC ............. G06T 2207/30244; G06T 7/74; G06T 2207/10012; G06T 2207/10024; G06T 2207/10028; G06T 2207/10072; G06T 2207/10116; G06T 2207/10132; G06T 2207/20076; G06T 2207/20084; G06T 2207/30021; G06T 2207/30061; G06T 2207/30096; A61B 6/545; A61B 6/547; A61B 6/542; A61B 6/587; A61B 6/588; A61B 6/589; A61B 6/54; A61B 6/4441
See application file for complete search history.

(56) References Cited

U.S. PATENT DOCUMENTS

| | | | | |
|---|---|---|---|---|
| 2016/0296183 | A1 | 10/2016 | Flohr et al. | |
| 2018/0168534 | A1 | 6/2018 | Desponds | |
| 2018/0350081 | A1* | 12/2018 | Hsieh | G06T 7/248 |
| 2019/0180482 | A1 | 6/2019 | Takahashi et al. | |
| 2019/0206069 | A1 | 7/2019 | Buerger et al. | |
| 2020/0003704 | A1 | 1/2020 | Illemann et al. | |
| 2022/0031273 | A1* | 2/2022 | Lewis | A61B 6/527 |
| 2022/0061781 | A1 | 3/2022 | Zhao | |
| 2022/0126117 | A1* | 4/2022 | Voronenko | A61N 5/1084 |
| 2023/0149741 | A1 | 5/2023 | Hirai et al. | |

FOREIGN PATENT DOCUMENTS

| | | | |
|---|---|---|---|
| CN | 107862715 | A | 3/2018 |
| CN | 111528890 | A | 8/2020 |
| CN | 111915494 | A | 11/2020 |
| KR | 20210147384 | A | 12/2021 |

* cited by examiner

400

METHOD AND SYSTEM FOR MEDICAL IMAGING

CROSS-REFERENCE TO RELATED APPLICATIONS

This application claims priority to the Chinese Patent Application No. 202211069678.6, filed on Sep. 1, 2022, Chinese Patent Application No. 202211152194.8, filed on Sep. 21, 2022, and Chinese Patent Application No. 202211608477.9, filed on Dec. 14, 2022, the contents of each of which are hereby incorporated by reference.

TECHNICAL FIELD

The present disclosure relates to a field of medical imaging, in particular, relates to systems and methods for determining imaging parameters.

BACKGROUND

In clinical practice, the disease development of a patient may be determined by performing multiple scans at different stages of the disease. Normally, the technician needs to set imaging parameters for each scan, and the multiple scans are often performed with different imaging parameters. However, the imaging parameters set by the technician cannot guarantee that a consistency of the medical images acquired in the multiple scans remains within a preset range, resulting in inherent differences between the medical images due to the difference in the imaging parameters (i.e., even if there is no change in a lesion site, there are differences in the medical images), which may affect a judgment of a degree of changes in the lesion site.

Therefore, it is desirable to provide systems and methods for medical imaging that can update imaging parameters automatically, quickly, and accurately, thereby improving a comparability between medical images obtained at different stages.

SUMMARY

One aspect of the present disclosure provides a system for medical imaging. The system may include at least one storage medium including a set of instructions; and at least one processor in communication with the at least one storage medium, wherein when executing the set of instructions, the at least one processor may be directed to cause the system to perform operations including: obtaining historical state information of a scanning region in a historical scan and current state information of the scanning region in a current scan to be performed; determining whether historical parameter values of one or more imaging parameters used in the historical scan need to be updated based on a comparison result between the historical state information and the current state information; in response to determining that the historical parameter values of the one or more imaging parameters used in the historical scan need to be updated, determining updated parameter values of the one or more imaging parameters based on the historical state information and the current state information; and directing a medical imaging device to perform the current scan based on the updated parameter values of the one or more imaging parameters.

In some embodiments, the historical state information and the current state information relate to at least one of: whether the scanning region is fixed by a fixing device, whether a distance between the scanning region and a radiation source of the medical imaging device is within a preset distance range, whether the scanning region has a preset posture, or whether a radiation ray filtering device is placed between the scanning region and the medical imaging device.

In some embodiments, the one or more imaging parameters include at least one of: a position parameter of one or more movable components of the medical imaging device, an exposure parameter, or an image post-processing parameter.

In some embodiments, the determining updated parameter values of the one or more imaging parameters based on the historical state information and the current state information comprises: determining first feature information of a first medical image captured in the historical scan; determining the updated parameter values of the one or more imaging parameters based on the historical state information and the current state information such that a similarity degree between the first feature information and second feature information of a second medical image captured in the current scan is within a preset range.

In some embodiments, the updated parameter values of the one or more imaging parameters are determined according to a process including one or more iterations, each of the one or more iterations includes: determining a predicted second medical image based on the current state information, the first medical image, and initial parameter values of the one or more imaging parameters using an image prediction model, the image prediction model being a trained machine learning model; determining whether a similarity degree between the first feature information and third feature information of the predicted second medical image is within the preset range; in response to determining that the similarity degree between the first feature information and the third feature information is out of the preset range, determining adjusted parameter values of the one or more imaging parameters based on the first feature information and the third feature information, and designating the adjusted parameter values as initial parameter values in a next iteration; or in response to determining that the similarity degree between the first feature information and the third feature information is within of the preset range, designating the initial parameter values of the one or more imaging parameters as the updated parameter values of the one or more imaging parameters.

In some embodiments, an input of the image prediction model includes the current state information, the first medical image, and the initial parameter values.

In some embodiments, the image prediction model is selected from a model library including image prediction models corresponding to different states based on the current state information, and the input of the image prediction model includes the first medical image and the initial parameter values.

In some embodiments, the determining updated parameter values of the one or more imaging parameters based on the historical state information and the current state information comprises: for each of at least part of the one or more imaging parameters, determining, based on a first medical image captured in the historical scan, a reference range of the imaging parameter; determining, based on the current state information and the historical state information, a candidate parameter value of the imaging parameter; and determining, based on the candidate parameter value, the updated parameter value of the imaging parameter that is within the reference range of the imaging parameter.

In some embodiments, the determining updated parameter values of the one or more imaging parameters based on the historical state information and the current state information comprises: determining the updated parameter values by processing the historical state information, the current state information, and the historical parameter values using a parameter prediction model, the parameter prediction model being a trained machine learning model.

In some embodiments, the operations further include: determining size information of the scanning region based on a medical image captured in the historical scan or the current scan by: obtaining a first optical image of the scanning region captured by an optical camera in the historical scan or the current scan; determining, based on the first optical image, an equivalent thickness of the scanning region along a traveling direction of radiation rays in the historical scan or the current scan; determining, based on the equivalent thickness, a first distance between a radiation source and a reference point of the scanning region; and determining, based on the first distance and the medical image, the size information of the scanning region.

In some embodiments, the determining, based on the first distance and the medical image, the size information of the scanning region comprises: obtaining a second distance between the radiation source and a detector along the traveling direction and reference size information of each detector unit of the detector; determining a correction coefficient based on the first distance, the second distance, and the reference size information; determining the size information based on the correction coefficient and the medical image.

In some embodiments, the determining, based on the equivalent thickness, a first distance between a radiation source and a reference point of the scanning region comprises: determining a third distance between the radiation source and a supporting device that supports the scanning region; determining a fourth distance from the reference point to the supporting device based on the equivalent thickness; and determining the first distance based on the third distance and the fourth distance.

Another aspect of the present disclosure provides a method for medical imaging. The method may include obtaining historical state information of a scanning region in a historical scan and current state information of the scanning region in a current scan to be performed; determining whether historical parameter values of one or more imaging parameters used in the historical scan need to be updated based on a comparison result between the historical state information and the current state information; in response to determining that the historical parameter values of the one or more imaging parameters used in the historical scan need to be updated, determining updated parameter values of the one or more imaging parameters based on the historical state information and the current state information; and directing a medical imaging device to perform the current scan based on the updated parameter values of the one or more imaging parameters.

Another aspect of the present disclosure provides a non-transitory computer readable medium, comprising at least one set of instructions, wherein when executed by one or more processors of a computing device, the at least one set of instructions causes the computing device to perform a method. The method may include obtaining historical state information of a scanning region in a historical scan and current state information of the scanning region in a current scan to be performed; determining whether historical parameter values of one or more imaging parameters used in the historical scan need to be updated based on a comparison result between the historical state information and the current state information; in response to determining that the historical parameter values of the one or more imaging parameters used in the historical scan need to be updated, determining updated parameter values of the one or more imaging parameters based on the historical state information and the current state information; and directing a medical imaging device to perform the current scan based on the updated parameter values of the one or more imaging parameters.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further describable in terms of exemplary embodiments. These exemplary embodiments are describable in detail with reference to the drawings. These embodiments are non-limiting exemplary embodiments, in which like reference numerals represent similar structures throughout the several views of the drawings, and wherein.

DETAILED DESCRIPTION

Figure 1:
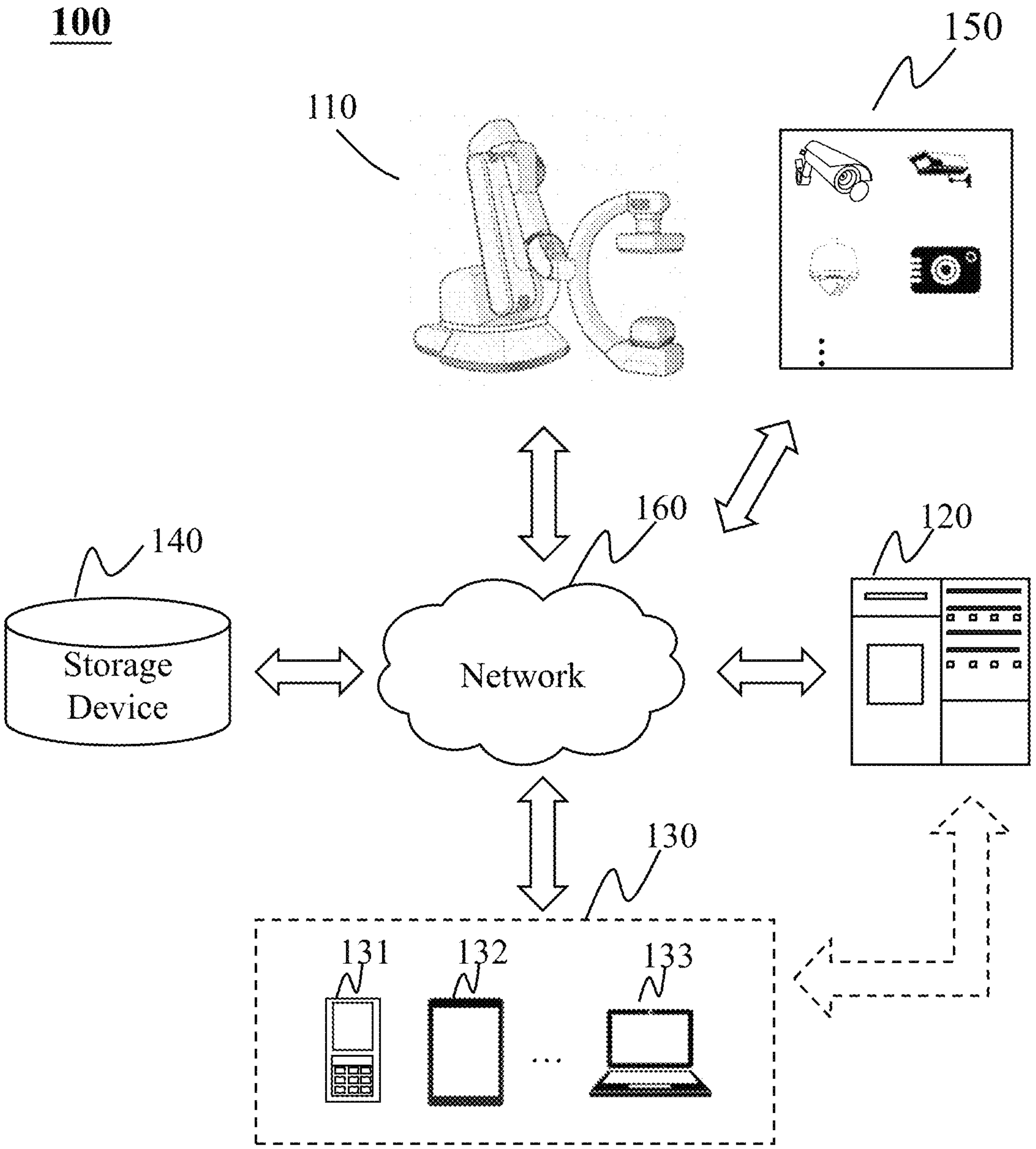
FIG. 1 is a schematic diagram illustrating an exemplary medical imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been describable at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assemblies of different levels in ascending order. However, the terms may be displaced by other expressions if they achieve the same purpose.

Generally, the word "module," "unit," or "block," as used herein, refers to logic embodied in hardware or firmware, or to a collection of software instructions. A module, a unit, or a block describable herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality describable herein may be implemented as software modules/units/blocks, but may be represented in hardware or firmware. In general, the modules/units/blocks describable herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure provides systems and methods for medical imaging. The systems may determine whether historical parameter values of one or more imaging parameters used in a historical scan need to be updated based on a comparison result between historical state information and current state information. In response to determining that the historical parameter values of the one or more imaging parameters used in the historical scan need to be updated, updated parameter values of the one or more imaging parameters may be determined based on the historical state information and the current state information, and a medical imaging device may be directed to perform the current scan based on the updated parameter values of the one or more imaging parameters. The systems may achieve automatic adjustment of the imaging parameters, thereby improving a comparability of medical images obtained in different scans.

In some embodiments, the systems may also determine a first distance between a radiation source and a reference point of a scanning region based on a first optical image of the scanning region, and determine size information of the scanning region based on the first distance and the medical image captured in a scan. The systems can achieve a size measurement of the scanning region easily and effectively without using reference objects with known dimensions or limiting the position of the measuring object (i.e., the scanning region).

In some embodiments, the systems may also determine a deflection degree of the scanning region relative to an extension direction of the supporting device based on a second optical image of the scanning region supported by the supporting device, and determine a rotation angle of the detector and/or the supporting device of the medical imaging device 110 based on the deflection angle, so that the scanning region is displayed in a forward direction in the medical image obtained during the scan. The systems may automatically rotate the detector and/or the supporting device to maintain a forward display of the scanning region in the medical image. An automatic rotation of the detector and/or the supporting device can avoid additional operations and exposure to radiation for workers.

FIG. 1 is a schematic diagram illustrating an exemplary medical imaging system according to some embodiments of the present disclosure. As shown in FIG. 1, a medical imaging system 100 may include a medical imaging device 110, a processing device 120, a terminal 130, a storage device 140, an optical camera 150, and a network 160.

The medical imaging device 110 may be configured to perform a scan on a scanning region of a scanning object to generate a medical image of the scanning region of the scanning object. The scanning object refers to humans or animals. The scanning region may be a whole body or a portion of the body. For example, the scanning region may include hand, feet, arm, leg, head, brain, heart, liver, spleen, lung, kidney, or any combination thereof. For the convenience of description, the terms "scanning object" and "patient" may be used interchangeably in the present disclosure.

In some embodiments, the medical imaging device 110 may include an X-ray imaging (XR) device, an X-ray computed tomography (CT) device, a direct digital X-ray imaging (DR) system, a magnetic resonance imaging (MR) device, a molecular imaging (e.g., a positron emission tomography/computed tomography (PET/CT), a positron emission tomography/magnetic resonance (PET/MR), or the like) device, an ultrasound imaging device, and an angiography (e.g., a digital subtraction angiography (DSA)) device. In some embodiments, the medical imaging device 110 may be a DSA device.

The processing device 120 may be configured to process information and/or data (e.g., status information, scanning data, medical images), and may also be configured to control the medical imaging device 110 and/or the optical camera 150.

In some embodiments, the processing device 120 may be configured to control the medical imaging device 110 to start, terminate, or continue the scan. In some embodiments, the processing device 120 may be configured to control the optical camera 150 to capture an optical image.

In some embodiments, the processing device 120 may be configured to direct the medical imaging device 110 to perform a scan based on determined parameter values of one or more imaging parameters. For example, the medical imaging device 110 may be a DR device, the medical imaging device 110 may include a gantry, a detector connected to the gantry, a radiation source for emitting X-rays, a movable arm connected to the radiation source, and a chest X-ray stand. When undergoing the scan, the scanning object needs to stand on a platform of the chest X-ray stand. The gantry may move freely on the ground of diagnosis and treatment room, and the detector may move relative to the gantry (e.g., lifting and rotating movements). The movable arm may be flexibly connected with various positions in the diagnosis and treatment room, or the movable arm may be an independent component. When the movable arm moves, the radiation source may be driven to move. Therefore, the processing device 120 may adjust a position of the detector by controlling the gantry, and adjust a position of the radiation source by controlling the movable arm, thereby adjusting gantry position parameters of the medical imaging device 110.

In some embodiments, the processing device 120 may obtain scanning data from the medical imaging device 110 (e.g., a CT device, etc.) and reconstruct medical images based on the scanning data. In some embodiments, the processing device 120 may directly obtain the medical images from the medical imaging device 110 (e.g., a DR system, etc.). In some embodiments, the processing device 120 may perform a post-processing on the medical images. For example, the processing device 120 may perform one or more operations such as noise reduction, super-resolution, sharpening, rotation, or the like, on the medical images. As another example, the processing device 120 may measure a true size (e.g., such as the length, the depth, the volume, or the like) of the scanning region based on the medical images. As a further example, the processing device 120 may divide (also known as segment) the medical image into at least two regions, such as regions of interest and other regions. As a further example, the processing device 120 may perform a three-dimension (3D) reconstruction of the scanning region based on the medical images.

In some embodiments, the processing device 120 may be a single server or a server group. The server group may be centralized or distributed. In some embodiments, the processing device 120 may be local or remote. In some embodiments, the processing device 120 may be implemented on a cloud platform. Merely for example, the cloud platform may include a private cloud, a public cloud, a hybrid cloud, a community cloud, a distributed cloud, an internal cloud, a multi-layer cloud, or any combination thereof. In some embodiments, the processing device 120 may be integrated or installed on the medical imaging device 110. For example, the processing device 120 may be fixed to the medical imaging device 110. In some embodiments, the processing device 120 may be integrated or installed on the optical camera 150. More descriptions of the processing device may be found elsewhere in the present disclosure, such as FIG. 3 and related descriptions.

The terminal 130 may be configured to receive information and/or data input by users and send the information and/or data to the processing device 120. The terminal 130 may interact with the users through a user interface. For example, the terminal 130 may receive clinical information input by the users through the user interface, wherein the clinical information may include gender, age, height, weight, heart rate of the patient, or any combination thereof. The clinical information may provide reference for related processes such as the scan and image post-processing, and specifically, patient feature information may be used to determine the imaging parameters. The clinical information may be input into the terminal 130 by the patient or others (e.g., doctors) with the authorization of the patient. For example, the terminal 130 may send a scanning request to the processing device 120 through the user interface.

The terminal 130 may be configured to display information and/or data to the users. For example, the terminal 130 may display the medical images and/or post-processing results of the medical images (e.g., measurement results, segmentation results, modeling results, etc.) through built-in or external display devices. For example, the terminal 130 may display the imaging parameters through the built-in or external display devices.

In some embodiments, the terminal(s) 130 may include a mobile device 131, a tablet computer 132, . . . , a laptop computer 133, or the like, or any combination thereof. For example, the mobile device 131 may include a mobile phone, a personal digital assistance (PDA), a laptop, a tablet computer, a desktop, or the like, or any combination thereof.

The storage device 140 may be configured to store information and/or data relating to the medical imaging system 100. For example, the storage device 140 may be configured to store a scanning protocol, imaging parameters, images (including medical and/or optical images), post-processing results of medical images, a trained machine learning model, system parameters, or the like. For example, the storage device 140 may be configured to store computer instructions for the processing device 120 to execute. When the processing device 120 executes computer instructions, methods such as an imaging control method, an image measurement method, and a rotation angle determination method may be implemented as provided in any embodiment of the present disclosure.

In some embodiments, the storage device 140 may include a hard disk, a magnetic tape, an optical disk, a flash memory, or any combination thereof.

The optical camera 150 may be configured to capture optical images of the patient's environment. For example, when the patient is lying on a supporting device (e.g., a scanning bed), the optical camera 150 may capture an optical image including the patient and the supporting device.

In some embodiments, the optical camera 150 may include an RGB camera, a gun type camera, a ball type camera, a portable camera, a depth camera, a structured light camera, or any combination thereof. In some embodiments, the optical camera 150 may be configured to capture three-dimensional (3D) optical images of the patient. In some embodiments, the medical imaging system 100 may include A plurality of optical cameras 150, and the image data collected by the plurality of optical cameras 150 may be configured to generate a 3D optical image or a model of the patient.

The optical camera 150 may be configured to obtain information about a region where the scanning object is located. In order to ensure that the optical camera 150 obtains the required information about the region where the scanning object is located, a shooting range of the optical camera 150 needs to cover the region where the medical imaging device 110 is located. In some embodiments, the optical camera 150 may be slidably and/or rotatably installed on floor, wall, ceiling, and other positions of the diagnosis and treatment room (e.g., the room where medical imaging device 110 is placed) to facilitate obtaining the information about the region where the scanning object is located. In addition, the optical camera 150 may be arranged at other positions that do not affect the scanning, as long as it can ensure that the shooting range can cover the region where the medical imaging device 110 is located. For example, the optical camera 150 may be rotatably installed on the ceiling, the corner, and other positions of the diagnosis and treatment room through a rotating component, and a complete region where the medical imaging device 110 is located may be captured by adjusting an angle. In some embodiments, the optical camera 150 may be mounted on the medical imaging device 110, for example, the tube of a DSA device.

The network 160 may include any suitable network that can facilitate the exchange of information and/or data for the medical imaging system 100. The network 160 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, switches, server computers, and/or any combination thereof. In some embodiments, the network 160 may include one or more network access points. For example, the network 160 may include wired and/or wireless network access points such as base stations and/or internet exchange points through which one or more components of the medical imaging system 100 may be connected to the network 160 to exchange data and/or information.

It should be noted that the above description regarding the medical imaging system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical imaging system 100 may include one or more additional components and/or one or more components of the medical imaging system 100 described above may be omitted. Additionally or alternatively, two or more components (e.g., the medical imaging device 110 and the processing device 120) of the medical imaging system 100 may be integrated into a single component. A component of the medical imaging system 100 may be implemented on two or more sub-components.

Figure 2:
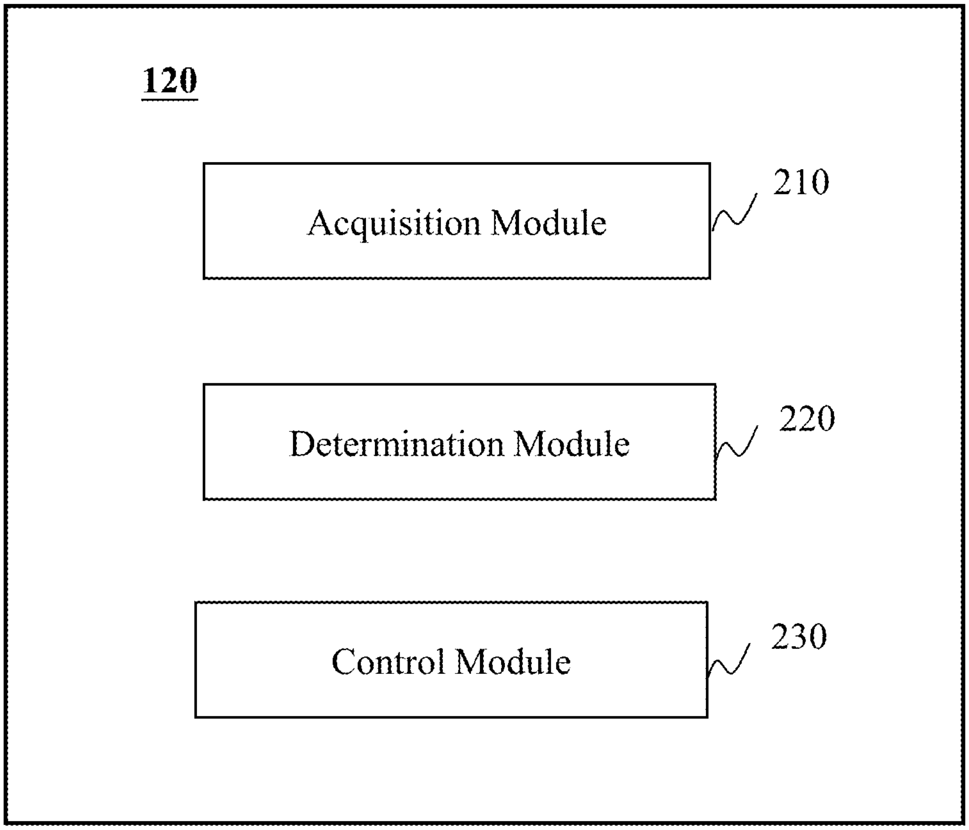
FIG. 2 is a block diagram illustrating an exemplary processing device according to some embodiments of the present disclosure.

FIG. 2 is a block diagram illustrating an exemplary processing device 120 according to some embodiments of the present disclosure. As illustrated in FIG. 2, the processing device 120 may include an obtaining module 210, a determination module 220, and a controlling module 230.

The obtaining module 210 may be configured to obtain historical state information of a scanning region in a historical scan and current state information of the scanning region in a current scan to be performed.

The determination module 220 may be configured to determine whether historical parameter values of one or more imaging parameters used in the historical scan need to be updated based on a comparison result between the historical state information and the current state information. In response to determining that the historical parameter values of the one or more imaging parameters used in the historical scan need to be updated, the determination module 220 may be also configured to determine updated parameter values of the one or more imaging parameters based on the historical state information and the current state information.

In some embodiments, the determination module 220 may also be configured to determine size information of the scanning region based on a medical image of the scanning region. More description of determining the size information of the scanning region may be found elsewhere in the present disclosure, such as FIG. 7 and related descriptions.

In some embodiments, determination module 220 may also be configured to determine a rotation angle of the supporting device and/or a detector of the medical imaging device 110 collected by optical camera 150. More descriptions of determining the rotation angle may be found elsewhere in the present disclosure, such as FIG. 10 and related descriptions.

The controlling module 230 may be configured to direct a medical imaging device to perform the current scan based on the updated parameter values of the one or more imaging parameters.

Figure 3:
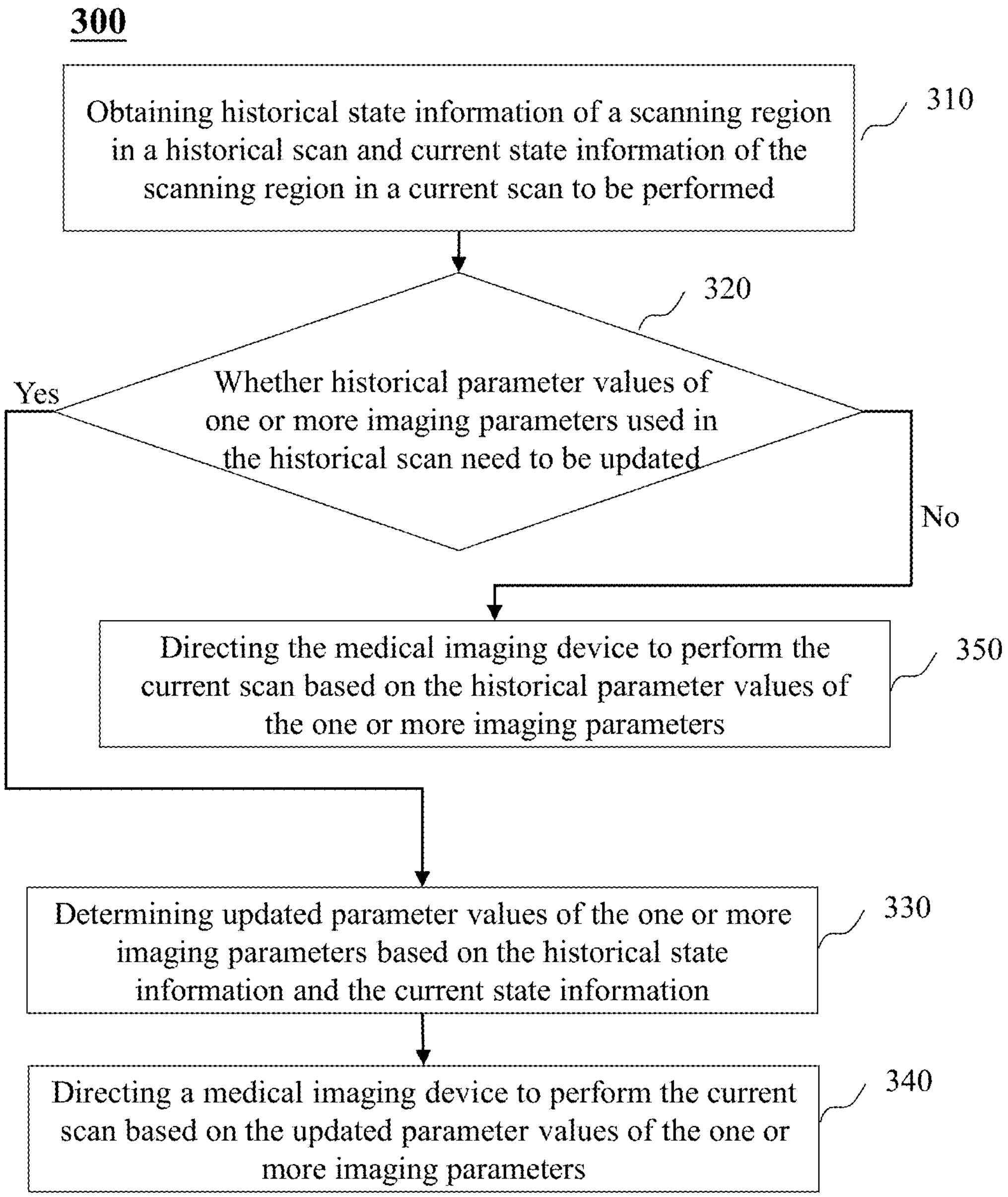
FIG. 3 is a flowchart illustrating an exemplary process for medical imaging according to some embodiments of the present disclosure.

More detailed descriptions of the modules in the processing device 120 may be found elsewhere in the present disclosure, for example, the descriptions of FIG. 3.

It should be noted that the above descriptions of the processing device 120 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 120 may include one or more other modules (e.g., a training module for training machine learning models) and/or one or more modules described above may be omitted. Additionally or alternatively, two or more modules may be integrated into a single module and/or a module may be divided into two or more units. However, those variations and modifications also fall within the scope of the present disclosure.

FIG. 3 is a flowchart illustrating an exemplary process for medical imaging according to some embodiments of the present disclosure. In some embodiments, a process 300 may be performed by the processing device 120 (e.g., a medical imaging system 200). As shown in FIG. 3, the process 300 may include the following operations.

In 310, historical state information of a scanning region in a historical scan and current state information of the scanning region in a current scan to be performed may be obtained. In some embodiments, the operation 310 may be performed by the obtaining module 210.

The state information refers to information that reflects a state of the scanning region in a scan. In some embodiments, the state information (e.g., the historical state information and the historical state information) may be related to one or more of the following states: whether the scanning region is fixed by a fixing device (e.g., a plaster cast, a neck bracket, an elbow joint fixation bracket, a knee joint fixation bracket, an ankle fixation bracket, etc.), whether a distance between the scanning region and a radiation source of the medical imaging device is within a preset distance range, whether the scanning region has a preset posture, whether a radiation ray filtering device is placed between the scanning region and the medical imaging device. The radiation ray filtering device may include a grid placed between the scanning region and a detector of the medical imaging device, a filter for filtering soft rays placed between the scanning region and a radiation source of the medical imaging device, etc.

In some embodiments, the processing device 120 may identify at least part of the state information based on the optical image obtained by the optical camera 150. For example, the processing device 120 may determine at least part of the historical state information based on an optical image captured before or during the historical scan. As another example, the processing device 120 may determine at least part of the current state information based on an optical image captured before or during the current scan.

In some embodiments, the optical image may be a 3D image. For example, the processing device 120 may determine whether the scanning region is in a plaster cast based on a 3D optical image including the scanning region obtained by the optical camera 150. For example, the processing device 120 may determine whether the medical imaging device includes a filter based on the 3D optical image including the medical imaging device 110 obtained by the optical camera 150.

In some embodiments, the optical image may be a depth image. The depth image may be also known as a range image, and the depth image refers to an image that include pixel values determined based on a distance (depth) value of each point in a scene collected by an image collector (e.g., a camera). Correspondingly, the optical camera 150 may include a depth camera, such as a structured light depth camera, a time flight depth camera, a binocular stereo camera, or the like. The processing device 120 may determine information of several feature points of the scanning object based on the depth image (e.g., positions of the feature points, corresponding regions of the feature points, etc.), and determine the status information of the scanning region based on the information of the feature points. The feature points refer to positioning points selected on the scanning object for labeling purposes. For example, the feature points may include the feature points used to mark regions of the human body such as head, shoulder, neck, elbow, wrist, ankle, knee, or the like. A combination of the plurality of feature points may be used to represent specific regions of the human body. The processing device 120 may determine posture information of the scanning region based on the information of the plurality of feature points of the scanning object, and determine whether the scanning region has a preset posture.

In some embodiments, the processing device 120 may identify one or more states of the scanning region by using an image recognition algorithm to process the optical image containing the scanning region captured by the optical camera 150, such as whether the scanning region is in the plaster cast (such as whether the left leg is in the plaster cast), whether the scanning region is fixed by a fixing device (such as whether the neck is fixed by a neck brace), or the like. In some embodiments, the image recognition algorithm may include a trained machine learning model, which may be also known as an image recognition model. The processing device 120 may train an initial model based on sample images collected in real scenes to obtain an image recognition model. In some embodiments, the image recognition model may also be generated by other devices.

Merely for example, the machine learning models mentioned in the present disclosure may include one or more models such as a linear regression model, a logistic regression model, a neural network (e.g., a deep learning model), or the like.

In some embodiments, when the status information includes whether the scanning region is in the plaster cast, the status information may also include a thickness of the plaster. In some embodiments, the processing device 120 may determine a thickness of the plaster based on the optical image containing the scanning region. For example, if the scanning region is the left leg and the left leg is in the plaster cast while the right leg is not in the plaster cast, the processing device 120 may obtain a thickness of the plaster cast of the left leg by identifying a radius of the left leg and a radius of the right leg based on the optical image, and subtracting the radius of the right leg from the radius of the left leg. As another example, the processing device 120 may identify a position of the left leg where the radius changes suddenly based on the optical image and determine the thickness of the plaster cast based on the change of the radius at the identified position.

In some embodiments, the processing device 120 may identify position information of the scanning region and position information of the radiation source (e.g., an X-ray generating device) based on the information of the region where the scanning object is located, determine a distance between the scanning region and the radiation source, and determine whether the distance between the scanning location and the radiation source is within a preset distance range. In some embodiments, the preset distance range may be manually determined based on experience.

In some embodiments, the processing device 120 may determine positions of several feature points of the scanning object and determine the posture of the scanning region based on the positions of the plurality of feature points. For example, when the scanning region is the leg, the feature points associated with the leg may include key points corresponding to the ankle, the knee, the calf, the thigh, or the like. When an angle between a connecting line between the key points corresponding to the knee and ankle and a connecting line between the key points corresponding to the knee and thigh is less than or equal to 45 degrees, the scanning region may be considered as holding a knee joint flexion posture. The processing device 120 may perform a point set registration on the posture of the scanning region and the preset posture, and determine whether the scanning region has the preset posture based on the registration result. For example, the processing device 120 may perform a rigid motion transformation (e.g., rotation, translation) on a first point set representing the scanning region, and determine an overlapping probability between the points in a transformed first point set and the points in a second point set representing a preset posture. The processing device 120 may further determine whether the overlapping probability exceeds a first preset threshold to identify whether the scanning region holds a standard posture. If the overlapping probability exceeds the first preset threshold, the processing device 120 may determine that the scanning region holds the preset posture. Otherwise, the processing device 120 may determine that the scanning region does not hold the preset posture.

In some embodiments, the processing device 120 may identify the scanning region and the detector of the medical imaging device 110 in the optical image captured by the optical camera 150, and identify whether a grid is arranged between the scanning region and the detector based on the optical image.

In some embodiments, the processing device 120 may identify the medical imaging device 110 in the optical image captured by the optical camera 150, and identify whether the medical imaging device 110 includes a filter based on the optical image.

In 320, whether historical parameter values of one or more imaging parameters used in the historical scan need to be updated may be determined based on a comparison result between the historical state information and the current state information. In some embodiments, the operation 320 may be performed by the determination module 220.

In some embodiments, the one or more imaging parameters may include at least one of: a position parameter of one or more movement components of the medical imaging device, an exposure parameter, or an image post-processing parameter. In some embodiments, the one or more movement components may include a gantry, a detector, a scanning table, a radiation source, or any combination thereof.

The position parameter of the gantry of the medical imaging device may include a distance (e.g., a source to image receiver distance (SID)) between the radiation source (e.g., an X-ray tube) and the detector (e.g., an image receiver), a rotation angle (RVA) of the radiation source around a vertical axis, a rotation angle (RHA) of the radiation source around a horizontal axis, or any combination thereof. Different position parameters of the gantry of the medical imaging devices may affect image quality, for example, the SID may affect an attenuation of the radiation dose, the RVA and RHA may affect an imaging angle of the scanning region. Exemplary exposure parameters may include a voltage, a current, a time, a current time product, a filter gate type, a filtering, a focal point, a size and a position of automatic exposure control (AEC), a field of View (FOV), or any combination of thereof. The exposure parameters may be configured to control radiation conditions such as an X-ray dose, an X-ray hardness, and an exposure time during scanning, which may directly affect the quality of medical images and clinical diagnosis. The image post-processing parameter may include a window width, a window level, a brightness, an enhancement, a contrast, or any combination thereof. The image post-processing parameters may directly affect the post-processing effect of the medical images.

A historical parameter value refers to an imaging parameter value used in historical scanning. In some embodiments, when the current state information has not changed compared to the historical state information or the current state information has changed slightly compared to the historical state information, the processing device 120 may determine that the historical parameter values of the one or more imaging parameters do not need to be updated. Specifically, the processing device 120 may determine whether the current state information has changed compared to the historical state information. If it is determined that the current state information does not change compared to the historical state information, the processing device 120 may determine that the historical parameter values of the imaging parameter(s) do not need to be updated. If it is determined that the current state information changes compared to the historical state information, the processing device 120 may further determine whether a change in the current state information compared to the historical state information is small (e.g., whether a similarity degree between the current state information and the historical state information exceeds a preset threshold). If it is determined that the current state information has changed significantly compared to the historical state information (e.g., the similarity degree does not exceed the preset threshold), the processing device 120 may determine that the historical parameter values of the imaging parameter(s) need to be updated. If determining that the current state information has a small change compared to the historical state information (e.g., the similarity degree exceeds the preset threshold), the processing device 120 may determine that the historical parameter values of the imaging parameter(s) do not need to be updated.

In some embodiments, as long as the current state information changes compared to the historical state information, the processing device 120 may determine that the historical parameter values of the imaging parameter(s) need to be updated.

In response to determining that the historical parameter values of the imaging parameter(s) need to be updated, the processing device 120 may perform the operations 330 and 340.

In 330, updated parameter values of the one or more imaging parameters may be determined based on the historical state information and the current state information. In some embodiments, the operation 330 may be performed by the determination module 220.

In some embodiments, the processing device 120 may determine first feature information of a first medical image captured in the historical scan. Further, the processing device may determine the updated parameter values of the one or more imaging parameters based on the historical state information and the current state information such that a similarity degree between the first feature information and second feature information of a second medical image captured in the current scan (also referred to as an image consistency) is within a preset range. The first feature information and the second feature information may be related to a radiation incidence center, a radiation incidence angle, an image feature parameter, or the like. The image feature parameter may include a window width (reflecting contrast information of the image), a window level (reflecting brightness information of the image), a contrast, a signal-to-noise ratio, and other parameters that affect visual presentation of the image. In some embodiments, the image consistency may include a consistency between original medical images and/or a consistency between processed medical images. The consistency between original medical images refers to the similarity degree determined based on the radiation incidence center and/or the radiation incidence angle, while the consistency between processed medical images refers to the similarity degree determined based on the one or more image feature parameters such as a window width (reflecting contrast information of the image), a window level (reflecting brightness information of the image), a contrast, or the like.

In some embodiments, the processing device 120 may pre-store a parameter comparison table, which may include a plurality of records. Each record may include reference historical state information, reference current state information, reference historical parameter values of the imaging parameter(s), and reference current parameter values of one or more imaging parameters. In order to generate the parameter comparison table, the processing device 120 (or other devices) may measure an impact of different state information on the relevant indicators of the image consistency under different parameter conditions, and determine parameter change values required to eliminate the impact. Furthermore, the processing device 120 may generate the parameter comparison table based on the parameter change values under different parameter conditions. It should be understood that the historical parameter values and updated parameter values of one or more imaging parameters may be equal, that is, only the historical parameter values of parts of the imaging parameters need to be updated. The parameter comparison table may also be generated by other devices.

For example, if the historical state information indicates that the scanning region is in the plaster cast, and the current state information indicates that the scanning region is not in the plaster cast, since whether the scanning region is in the plaster cast may affect a dose of X-rays, the processing device 120 may adjust the exposure parameters to ensure that the consistency between the second medical image and the first medical image is within the preset range. The processing device 120 (or other devices) may measure a dose attenuation caused by thicknesses of the different plasters at different voltages and determine a current increment required to compensate for the attenuation. Furthermore, the processing device 120 may generate a parameter comparison table based on the current increment under different parameter conditions. After saving the parameter comparison table, the processing device 120 may lookup the parameter comparison table based on the historical parameter values of the imaging parameter(s) (e.g., the voltage and current), the thickness of plaster in the historical state information (e.g., a mm), and the thickness of plaster in the current state information (e.g., 0 mm), thereby obtaining the updated parameter values of the one or more imaging parameters (e.g., the voltage and current).

As another example, whether the scanning region is fixed by the fixing device may affect the dose of X-rays. In addition, a metal fixing device may affect an average grayscale value of images. The processing device 120 may adjust the exposure parameter and image post-processing parameter to ensure that the image consistency between the second medical image and the first medical image is within the preset range.

As a further example, whether a distance between the scanning region and the X-ray generating device is within a preset distance range may affect the dose of X-rays. The processing device 120 may adjust the exposure parameter to ensure that the image consistency between the second image and the first medical image is within the preset range.

As a further example, whether the scanning region has a preset posture may affect the SID (indirectly affecting the X-ray dose), the X-ray incidence center, and the X-ray incidence angle. The processing device 120 may adjust the position parameter of the gantry of the medical imaging device to ensure that the image consistency between the second medical image and the first medical image is within the preset range.

As a further example, whether a grid is arranged between the scanning region and the receiving device and whether the scanning device includes a filter may be determined. When the grid and the filter exist, a model of the grid and/or filter may affect the dose of X-rays. The processing device 120 may adjust the exposure parameter to ensure that the image consistency (e.g., a dose similarity) between the second medical image, and the first medical image is within the preset range. The model of the grid may include different gate periods, gate densities (e.g., 31-110 lines/cm), and grid ratios (e.g., 4:1-16:1). The model of the filter may include a thickness of the filter (e.g., 0.1 mm, 0.2 mm, 0.3 mm, etc.).

In some embodiments, the processing device 120 may determine the updated parameter values by processing the historical state information, the current state information and the historical parameter values using a parameter prediction model, wherein the parameter prediction model is a trained machine learning model. In some embodiments, the input of the parameter prediction model may include the historical state information, the current state information, and the historical parameter values of the imaging parameter(s), and the output of the parameter prediction model may include the updated parameter values of the one or more imaging parameters.

In some embodiments, the input of the parameter prediction model may include the historical state information, the current state information, and the historical parameter values of the imaging parameter(s), and the output of the parameter prediction model may include changes in one or more imaging parameters. For each imaging parameter, the processing device 120 may superimpose the change of the imaging parameter on the historical parameter value of the imaging parameter to obtain the updated parameter value of the imaging parameter.

In some embodiments, the processing device 120 may determine a plurality of training samples for training an initial model based on data (e.g., state data, historical parameter values of the imaging parameter(s)) relating to a plurality of pairs of historical scans, and obtain the parameter prediction model by training the initial model using the training samples. The image consistency between medical images obtained from each pair of historical scans may be within the preset range. Each training sample may correspond to a pair of historical scans, wherein state information and imaging parameter values of a previous historical scan and state information of a subsequent historical scan may be used as training inputs, and parameter values or parameter value changes of the subsequent historical scan may be used as training labels. In some embodiments, the parameter prediction model may also be generated by other devices.

In some embodiments, for each imaging parameter among the one or more imaging parameters, the processing device 120 may determine a reference range (or update range) of the imaging parameter based on the first medical image, and determine candidate parameter values of the imaging parameter based on the historical state information and the current state information. Furthermore, for each of the one or more imaging parameters, the processing device 120 may determine the updated parameter value of the imaging parameter located within the reference range based on the candidate parameter values of the imaging parameter. More descriptions of determining the updated parameter value of the imaging parameter may be found elsewhere in the present disclosure, such as FIG. 4 and related descriptions.

In some embodiments, the updated parameter values of the one or more imaging parameters may be determined according to a process including one or more iterations. More descriptions of each iteration may be found elsewhere in the present disclosure, such as FIG. 5 and related descriptions.

In 340, the medical imaging device 110 may be directed to perform the current scan based on the updated parameter values of the one or more imaging parameters. In some embodiments, the operation 340 may be performed by the control module 230.

In response to determining that the historical parameter values of the one or more imaging parameters used in the historical scan do not need to be updated, the processing device 120 may perform operation 350.

In 350, the medical imaging device 110 may be directed to perform the current scan based on the historical parameter values of the one or more imaging parameters. In some embodiments, the operation 340 may be performed by the control module 230.

The processing device 120 or terminal 130 may display the first medical image obtained in the historical scan and the second medical image obtained in the current scan for comparison.

In some embodiments, the processing device 120 may determine a region of interest in a medical image based on protocol information of the patient and pre-stored protocol information in a radiology information system (RIS). The medical image may be a medical image obtained in any scan, such as the first medical image obtained in the historical scan or the second medical image obtained in the current scan.

In some embodiments, the protocol information of the patient may include the patient's name, the examination region, the diagnosis result, or the like. The pre-stored protocol information may include key examination regions corresponding to different diagnostic results stored in advance.

The region of interest (ROI) of the medical image refers to a region that needs to pay attention to in the medical image. For example, it is assumed that the examination regions of the patient A and the patient B are both the lungs. If the diagnostic result of the patient A indicates that the patient A has tumor, the region of interest of the patient A may be hilum of the lungs. If the diagnostic result of the patient B is pneumonia, the region of interest of the patient B may be lung marking. In some embodiments, the processing device 120 may segment the ROI from the medical image to generate a segmentation image of the ROI. In the segmentation image, a first pixel value corresponding to the region of interest (e.g., the hilum of the lung) may be different from a second pixel value corresponding to other regions, for example, the first pixel value may be 1 and the second pixel value may be 0.

In some embodiments, the processing device 130 may generate an ROI segmentation image based on the protocol information of the patient, the pre-stored protocol information, and the medical image by using an ROI recognition model. More descriptions of determining the ROI of the medical image may be found elsewhere in the present disclosure, such as FIG. 6 and related descriptions.

Through the process 300, the automatic adjustment of imaging parameters can be achieved, manual intervention can be reduced, and the efficiency and accuracy of parameter settings can be improved. On the other hand, since the updated imaging parameters can ensure that the consistency between the second medical image and the first medical image meets a preset requirement, image differences caused by factors other than physiological structural changes (e.g., the setting of scanning parameters) can be avoided, thereby improving the comparability of medical images obtained in different scans.

In some embodiments, the processing device 120 may determine size information of the scanning region based on a medical image (e.g., the first medical image or the second medical image). For example, the processing device 120 may obtain a first optical image of the scanning region captured by an optical camera in the historical scan or the current scan. The processing device 120 may determine an equivalent thickness of the scanning region along a traveling direction of radiation rays in the historical scan or the current scan based on the first optical image. The processing device 120 may further determine a first distance between a radiation source and a reference point of the scanning region based on the equivalent thickness, and determine the size information of the scanning region based on the first distance and the medical image. More descriptions of determining the size information of the scanning region may be found elsewhere in the present disclosure, such as FIG. 7-FIG. 9 and related descriptions.

In some embodiments, before performing the historical scan or the current scan, the processing device 120 may adjust a supporting device and/or a detector of the medical imaging device such that such that a representation of the scanning region has a preset direction in the medical image collected in the historical scan or the current scan. Taking the current scan for instance, the processing device 120 may obtain a second optical image of the scanning region that is supported by a supporting device, the second optical image being captured by an optical camera before the current scan is performed. The processing device 120 may determine a deflection angle of the scanning region with respect to an extension direction of the supporting device based on the second optical image. The processing device 120 may further determine a rotation angle of the supporting device and/or a detector of the medical imaging device based on the deflection angle such that a representation of the scanning region in a second medical image captured in the current scan has the preset direction in the second medical image. More description of determining the rotation angle may be found elsewhere in the present disclosure, such as FIG. 10-FIG. 12B.

Figure 4:
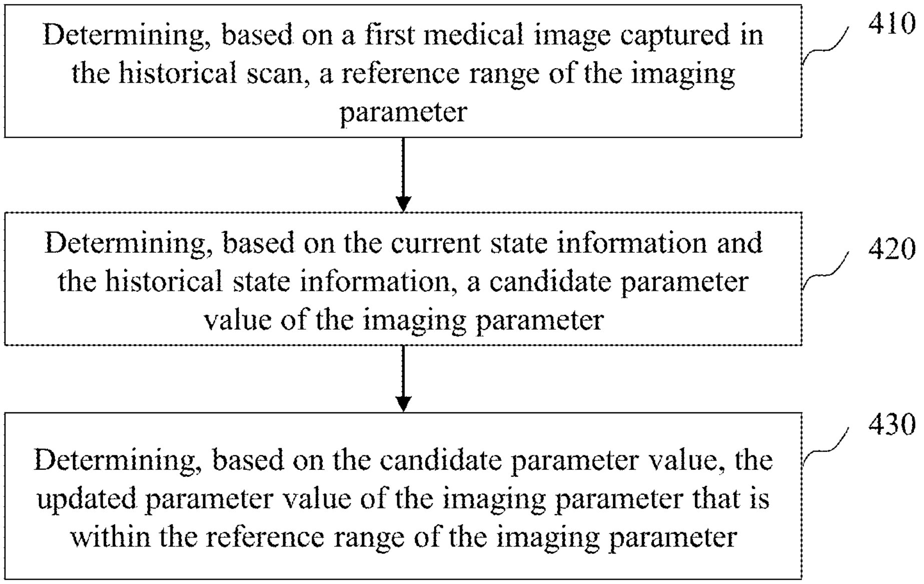
FIG. 4 is a flowchart illustrating an exemplary process for determining an updated parameter value of an imaging parameter according to some embodiments of the present disclosure.

FIG. 4 is a flowchart illustrating an exemplary process for determining an updated parameter value of an imaging parameter according to some embodiments of the present disclosure. In some embodiments, the process 400 may be performed for each of at least part of the one or more imaging parameters as described in connection with FIG. 3.

In 410, a reference range of the imaging parameter may be determined based on a first medical image captured in the historical scan.

In some embodiments, the processing device 120 may determine the reference range of the imaging parameter based on one or more image feature parameters of the first medical image. The image feature parameters refer to parameters that affect a visual presentation of medical images. For example, the image feature parameters may include grayscale, brightness, sharpness, contrast, signal-to-noise ratio, or the like. In some embodiments, the image feature parameters of the first medical image refer to image feature parameters of all regions of the first medical image. In some embodiments, the image feature parameters of the first medical image refer to image feature parameters of a region of interest of the first medical image. More descriptions of determining the region of interest may be found elsewhere in the present disclosure, such as FIG. 6 and related descriptions. The image feature parameters of the region of interest of the first medical image and the image feature parameters of all regions of the first medical image may be different (e.g., average grayscale values may be different). The image feature parameters of the region of interest of the first medical image may be more important for parameter updating, and the reference range of the imaging parameter determined based on the image feature parameters of the region of interest has a relatively higher accuracy.

In some embodiments, the processing device 120 may determine the reference range of the imaging parameter based on a mapping relationship between the image feature parameters of the first medical image and the reference range of the imaging parameter. For example, the processing device 120 may search for the reference range of the imaging parameter corresponding to the image feature parameters (e.g., the brightness) of the first medical image in a parameter range determination table, wherein the parameter range determination table may store reference ranges of the imaging parameter corresponding to different image feature parameters.

In some embodiments, the processing device 120 may input the first medical image into a parameter range prediction model to obtain a reference range of the imaging parameter. The parameter range prediction model may be a trained machine learning model. The processing device 120 may train an initial model based on a plurality of sample medical images and reference ranges of imaging parameters annotated for each sample medical image to obtain a parameter range prediction model. In some embodiments, the parameter range prediction model may be generated by other devices.

In 420, a candidate parameter value of the imaging parameter may be determined based on the current state information and the historical state information.

In some embodiments, the processing device 120 may determine the candidate parameter value based on the historical state information and the current state information in a similar manner as how the updated parameter value of the imaging parameter is determined as described in connection with operation 330. For example, the candidate parameter value of the imaging parameter may be determined based on the parameter comparison table or the parameter prediction model.

In 430, the updated parameter value of the imaging parameter that is within the reference range of the imaging parameter may be determined based on the candidate parameter value.

In some embodiments, the processing device 120 may determine a parameter value within the reference range of the imaging parameter that is closest to the candidate parameter value as the updated parameter value of the imaging parameter. For example, assuming that a reference range of a voltage parameter is a kV~b kV, a candidate parameter value of the voltage parameters is c kV, and $c<a$, the processing device 120 may determine that an updated parameter value of the voltage parameter may be a kV. As another example, assuming the reference range of the voltage parameter is a kV~b kV, the candidate parameter value of the voltage parameter is c kV, and $a<c<b$, the processing device 120 may determine that the updated parameter value of the voltage parameter may be c kV.

Figure 5:
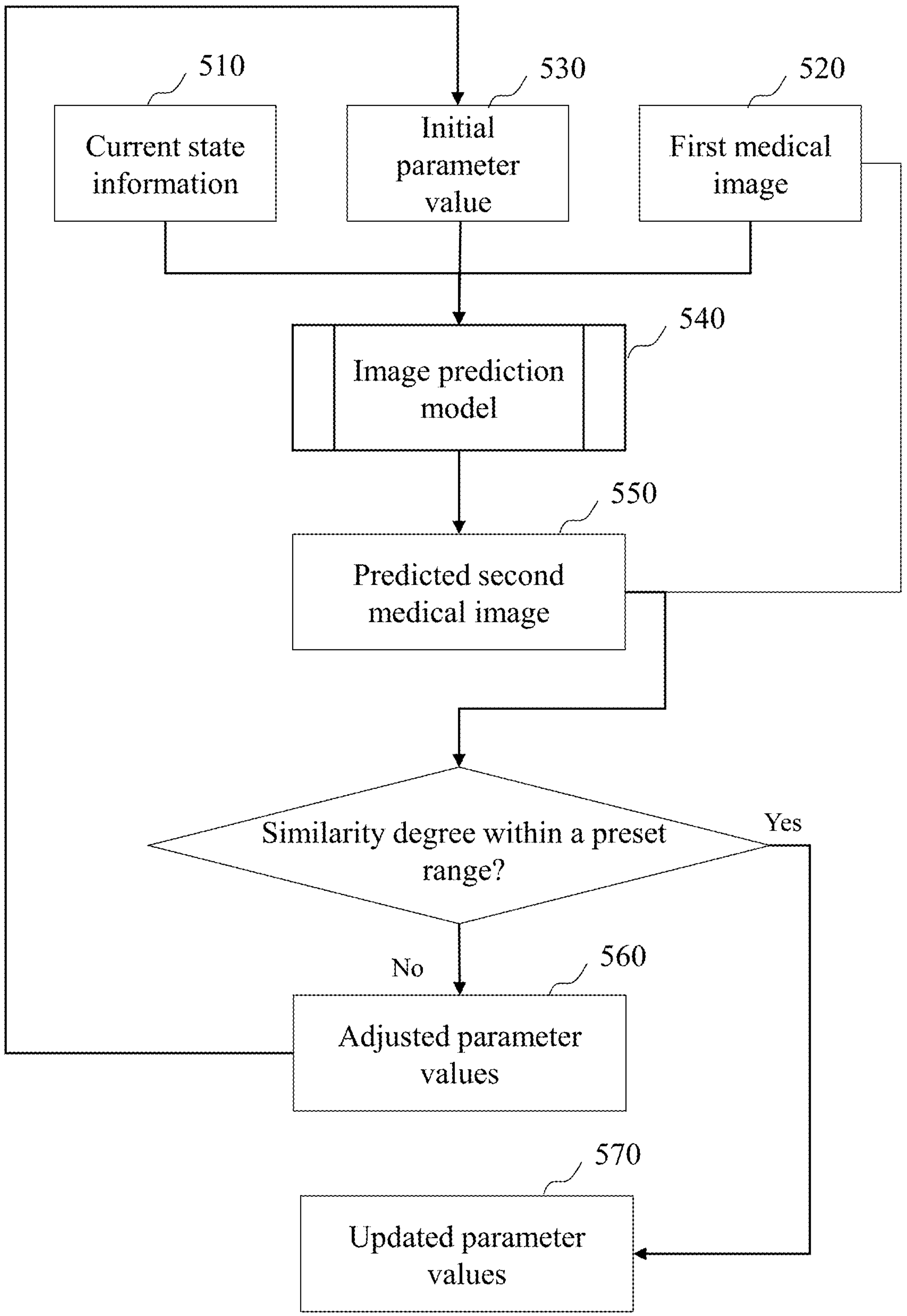
FIG. 5 is a schematic diagram illustrating an exemplary process for updating parameter values according to some embodiments of the present disclosure.

FIG. 5 is a schematic diagram illustrating an exemplary process for updating parameter values according to some embodiments of the present disclosure.

As shown in FIG. 5, the processing device 120 may determine the updated parameter values of the one or more imaging parameters according to a process including one or more iterations. Each iteration may include the following operations. The processing device 120 may determine a predicted second medical image 550 using an image prediction model 540 based on current state information 510, a first medical image 520, and initial parameter values 530 of the one or more imaging parameters, wherein the image prediction model 540 may be a trained machine learning model. The processing device may determine whether a similarity degree between first feature information of the first medical image 520 and third feature information of the predicted second medical image 550 (i.e., an image consistency between the first medical image 520 and the predicted second medical image 550) is within the preset range. In response to determining that the similarity degree between the first feature information and the third feature information is out of the preset range, the processing device 120 may determine adjusted parameter values 560 of the one or more imaging parameters based on the first feature information and the third feature information. For example, the processing device 120 may determine an adjusted direction of an imaging parameter (e.g., increase or decrease) based on a difference between the first feature information and the third feature information, and adjust the initial parameter value of the imaging parameter along the adjusted direction according to a preset step (increase or decrease the initial parameter value by the preset step size) to obtain the adjusted parameter value of the imaging parameter. After the parameter values of all the one or more imaging parameters are adjusted, the processing device 120 may designate the adjusted parameter values 560 of the one or more imaging parameters as the initial parameter values 530 of the one or more imaging parameters in a next iteration. In response to determining that the similarity degree between the first feature information and the third feature information is within the preset range, the processing device 120 may designate the initial parameter values 530 of the one or more imaging parameters in the current iteration as the updated parameter values 570 of the one or more imaging parameters, and stop the one or more iterations. In some embodiments, only the parameter values of a portion of the imaging parameter(s) may be adjusted, and the updated parameter values of these imaging parameters may be equal to their respective initial parameter values.

In some embodiments, the image prediction model 540 may be used to predict a medical image of a subject acquired using specific parameter values of the imaging parameter(s) when the subject has a certain state. In some embodiments, the input of the image prediction model 540 may include the current state information 510, the first medical image 520, and the initial parameter values 530. The processing device 120 may train an initial model based on a plurality of training samples and training labels to obtain the image prediction model 540. A training label corresponding to each training sample may be a ground truth medical image of a sample subject acquired using sample parameter values when the sample subject has a sample state. Each training sample (i.e., the training input) may include the sample parameter values, sample state information corresponding to the sample state, and another medical image of the sample subject acquired using other parameter values when the sample subject has a state different from the sample state. The image prediction model 540 may also be generated by other devices.

In some embodiments, the image prediction model 540 may be selected from a model library based on the current state information, wherein the model library may include image prediction models corresponding to different states (or different state transitions). Correspondingly, the input of the image prediction model 540 may include the first medical image 520 and the initial parameter values 530. For example, the processing device 120 may train a first image prediction model corresponding to state A and a second image prediction model corresponding to state B, that is, the model library may include a first image prediction model and a second image prediction model. The first image prediction model may be configured to predict a medical image of an object with the state A, and the second image prediction model may be configured to predict a medical image of an object with the state B. A training label of the first image prediction model may include a ground truth medical image of a sample subject acquired when the sample subject has the state A, and a training label of the second image prediction model may include a ground truth medical image of a sample subject acquired when the sample subject has the state B. The training process of the image prediction models corresponding to different states may be similar to the training processes of other machine learning models (e.g., the ROI recognition model 620) disclosed herein.

Figure 6:
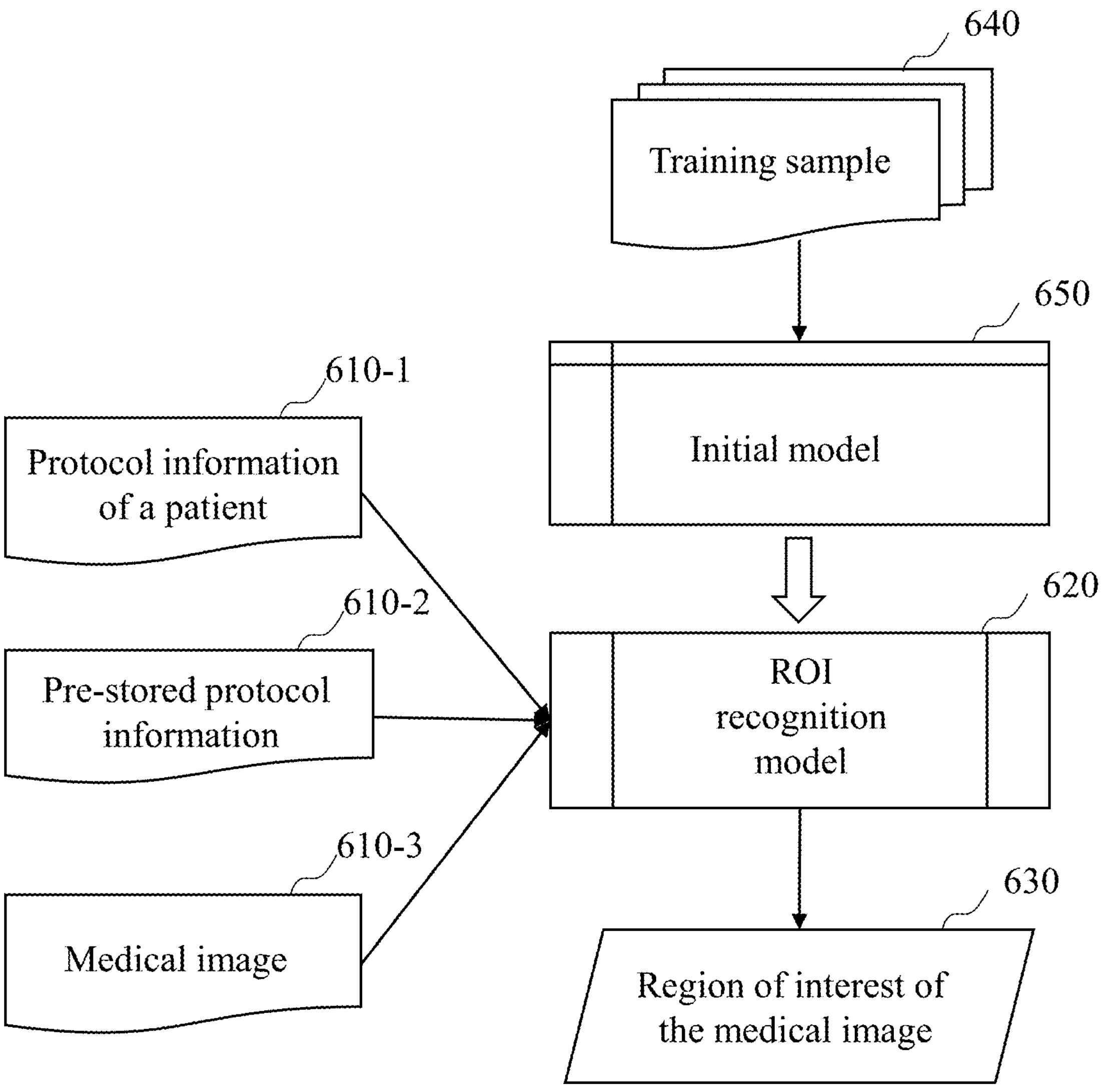
FIG. 6 is a flowchart illustrating an exemplary process of identifying a region of interest according to some embodiments of the present disclosure.

FIG. 6 is a flowchart illustrating an exemplary process of identifying a region of interest according to some embodiments of the present disclosure.

As shown in FIG. 6, the processing device 120 may input protocol information 610-1 of the patient, pre-stored protocol information 610-2, and a medical image 610-3 into an ROI recognition model 620, which may output an ROI 630 of the medical image 610-3. In some embodiments, the ROI 630 may be presented in the form of a binary segmentation image. For example, in the binary segmentation image 630, a pixel value corresponding to the region of interest may be 1 and pixel values corresponding to other regions may be 0. In some embodiments, the pre-stored protocol information 610-2 may be omitted.

In some embodiments, the ROI recognition model 620 may include a deep learning model. Merely for example, the deep learning models may include a convolutional neural network (CNN), a deep neural network (DNN), a recurrent neural network (RNN), or any combination thereof.

In some embodiments, as shown in FIG. 6, the processing device 120 may train the initial model 650 based on a plurality of training samples 640 to obtain the ROI recognition model 620. For example, each training sample 640 may include protocol information of a sample patient, the pre-stored protocol information, a sample medical image of the sample patient, and an ROI label. The ROI label may be a ground truth segmentation image of an ROI in the sample medical image. The ROI label may be manually calibrated.

A training process of the initial model 650 may include one or more iterations. Merely for example, in a current iteration, for each training sample 640, the processing device 120 may use an intermediate model to process the sample medical image of the training sample 640 to obtain a predicted ROI of the training sample 640. The intermediate model may be an initial model in the first iteration and may be a model generated in the previous iteration in other iterations. The processing device 120 may determine a value of the loss function based on the predicted ROI and the ROI label of the plurality of training samples 640 and update the intermediate model based on the value of the loss function.

The processing device 120 may iteratively update a model parameter based on the plurality of training samples 640 to ensure that the value of the loss function meets a preset condition, such as the value of the loss function converges, or the value of the loss function less than a preset value. When the value of the loss function meets the preset condition, the model training may be completed, and the processing device 120 may obtain the ROI recognition model 620 based on the final obtained model parameter.

Figure 7:
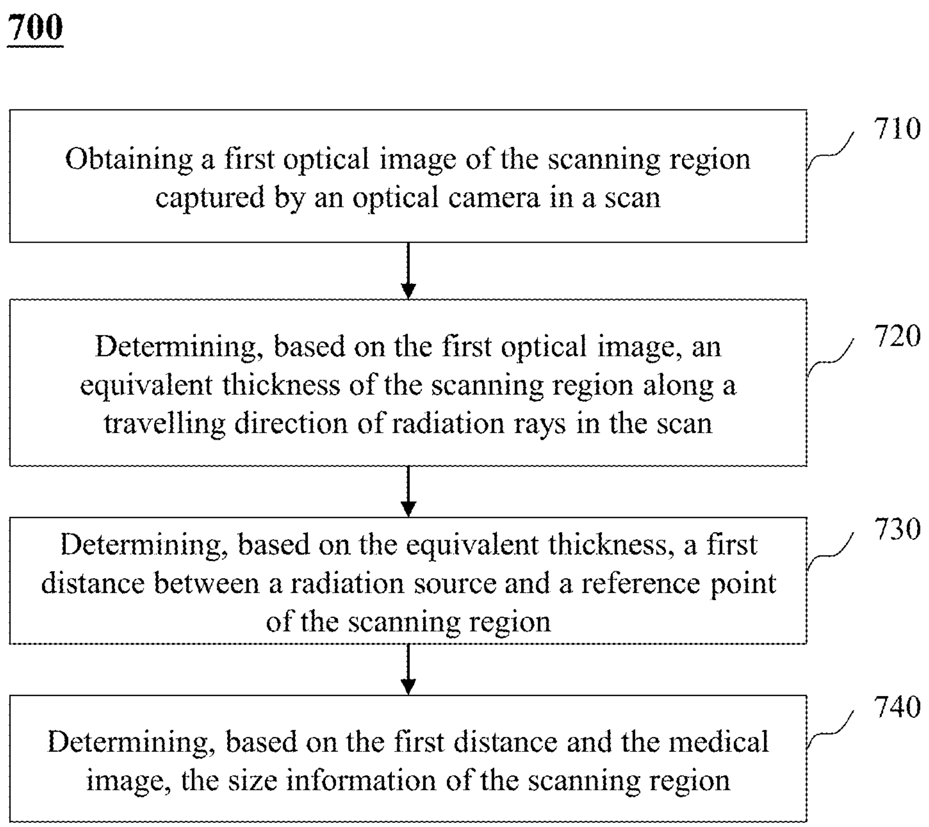
FIG. 7 is a flowchart illustrating an exemplary process for determining size information of a scanning region according to some embodiments of the present disclosure.

FIG. 7 is a flowchart illustrating an exemplary process for determining size information of a scanning region according to some embodiments of the present disclosure. A process 700 may be performed by the processing device 120 (e.g., the determination module 220). As shown in FIG. 7, the process 700 may include the following operations.

In 710, a first optical image of the scanning region captured by the optical camera 150 in a scan may be obtained.

The scan herein refers to any scan, such as the historical scan or current scan described in FIG. 3.

In some embodiments, the first optical image may be a two-dimension (2D) image or a three-dimension (3D) image. In some embodiments, the first optical image may include a plurality of 2D images collected from different angles. In some embodiments, the first optical image may be a depth image.

In some embodiments, the processing device 120 may obtain at least two candidate optical images collected by at least two (e.g., three) optical cameras, and select one from the least two candidate optical images. Furthermore, the processing device 120 may designate the selected candidate optical image as the first optical image. The processing device 120 may select the first optical image based on relevant information of the candidate optical images (e.g., clarity, brightness, authenticity, etc.).

In some embodiments, by setting the at least two optical cameras, when some optical cameras are damaged, the first optical image may still be obtained through the undamaged optical camera to ensure the subsequent operations.

In 720, an equivalent thickness of the scanning region along a traveling direction of radiation rays may be determined based on the first optical image.

Figure 8A:
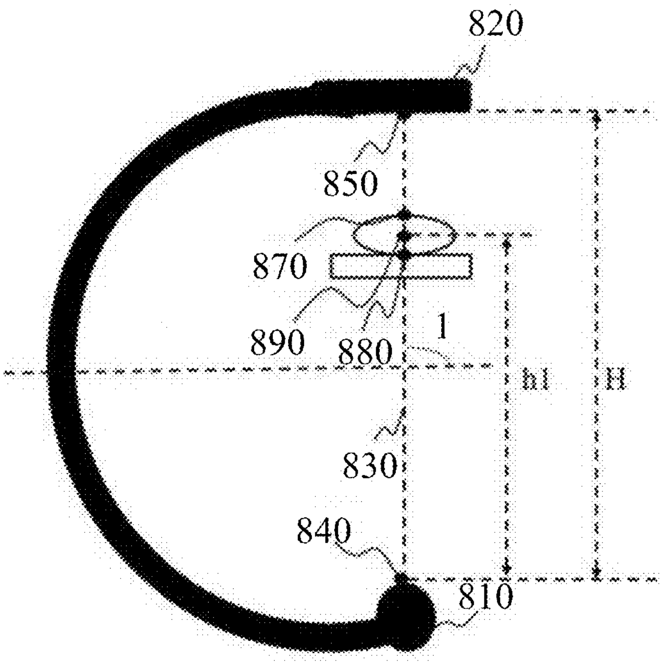
FIG. 8A is a schematic diagram illustrating an exemplary equivalent thickness of a scanning region along a traveling direction of radiation rays according to some embodiments of the present disclosure.
Figure 8B:
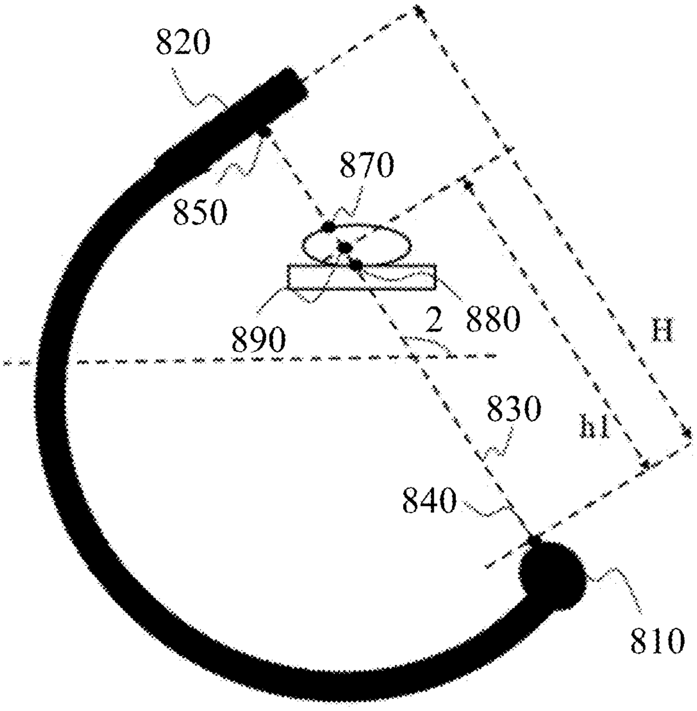
FIG. 8B is a schematic diagram illustrating an exemplary equivalent thickness of a scanning region along a traveling direction of radiation rays according to other embodiments of the present disclosure.

A focal point of the radiation source has a vertical projection point on the detector, and the traveling direction of radiation rays may be a direction from the focal point of the radiation source to the vertical projection point. When the radiation source and the detector rotate to different angles around a rotation center, the traveling direction of radiation rays may be different. For example, in FIGS. 8A and 8B, the traveling direction of radiation rays 830 may be a traveling direction from a focal point 840 of a radiation source 810 to a vertical projection point 850 on a detector 820. As shown in FIG. 8A, when the radiation source 810 and the detector 820 rotate around the rotation center to an angle 1, the traveling direction of radiation rays 830 may be a vertical direction. As shown in FIG. 8B, when the radiation source 810 and the detector 820 rotate around the rotation center to an angle 2, a certain angle may exist between the traveling direction of radiation rays 830 and the vertical direction.

In some embodiments, the processing device 120 may obtain the traveling direction of radiation rays from the medical imaging device 110. It should be understood that the radiation source and the detector are components of the medical imaging device 110, and the traveling direction of radiation rays determined by positions of the two components may be known information of the medical imaging device 110.

Taking FIGS. 8A and 8B as examples, the equivalent thickness of the scanning region along the traveling direction of radiation rays 830 may be a distance between points 870 and 880. When the radiation source and the detector rotate to different angles around the rotation center, the equivalent thicknesses of the scanning region along the traveling direction of radiation rays 830 may be different.

In some embodiments, the first optical image may be a 2D image, and the processing device 120 may determine a number of pixels in the first optical image that fall into the scanning region along the traveling direction of radiation rays, and determine the equivalent thickness of the scanning region along the traveling direction of radiation rays based on the number. For example, the equivalent thickness may be equal to the number multiplied by a transformation factor of the first optical image (wherein the correction factor may be associated with a transformation relationship between the image domain and the physical world). The equivalent thickness herein refers to a size in the real world rather than a size in the image.

In some embodiments, the processing device 120 may establish a 3D model of the scanning region based on the first optical image, and determine the equivalent thickness of the scanning region along the traveling direction of radiation rays based on the 3D model. In some embodiments, the first optical image may be a 3D image. In some embodiments, the first optical image may include a plurality of 2D images of the scanning regions collected from different angles. For example, the processing device 120 may reconstruct a depth image of the scanning region based on the plurality of 2D images collected from different angles by the optical camera 150, and establish a 3D model (e.g., a mesh model, a point cloud model) of the scanning region based on the depth image. The algorithm used for reconstructing the depth image may include a patch-based MVS (PMVS) algorithm, a marching cube (MC) algorithm, a dual contouring (DC) algorithm, or the like. In some embodiments, the processing device 120 may convert the reconstructed depth image into a 3D point cloud through a coordinate conversion, and establish a 3D model of the scanning region based on the 3D point cloud. In some embodiments, the first optical image may include a depth image of the scanning region.

In some embodiments, the processing device 120 may determine two contour points representing the thickness of the scanning region based on the traveling direction of radiation rays, and the two contour points may be intersection points of the traveling direction of radiation rays and the contour of the scanning region. The processing device 120 may designate a distance between the two contour points as the equivalent thickness of the scanning region along the traveling direction of radiation rays. Merely for example, taking the FIGS. 8A and 8B as examples, the thickness of the scanning region along the traveling direction of radiation rays 830 may be a distance between a contour point 870 and a contour point 880.

In 730, a first distance between a radiation source and a reference point of the scanning region may be determined based on the equivalent thickness.

The reference point may be any point in the scanning region along the traveling direction of radiation rays, such as a center point. Taking FIG. 8A as an example, when the radiation source 810 and the detector 820 rotate around the rotation center to the angle 1, a reference point 890 of the scanning region may be a center point of a connecting line between the contour point 870 and the contour point 880.

The first distance may be a distance between the reference point of the scanning region and the focal point of the radiation source. The first distance may be a distance in a real world rather than a distance in the image. Taking FIGS. 8A and 8B as examples, the first distance may be a distance between the point 890 and the focal point 840 of the radiation source 810. When the radiation source and the detector rotate to different angles around the rotation center, the first distance may be different.

In some embodiments, the first optical image may be a 2D image (e.g., a 2D image taken from the side view of the scanning region), and the processing device 120 may determine a connecting line between the reference point of the scanning region and the focal point of the radiation source in the first optical image, and determine the first distance based on the number of pixel points on the connecting line.

In some embodiments, the processing device 120 may also establish a 3D model of the medical imaging device 110 based on the optical image collected by the optical camera 150, fuse the 3D model of the medical imaging device 110 with the 3D model of the scanning region based on a spatial positional relationship, and determine a distance from the reference point of the scanning region to the focal point of the radiation source of the medical imaging device 110 based on the fused 3D model.

In some embodiments, the processing device 120 may determine a third distance between the radiation source and a supporting device that supports the scanning region, determine a fourth distance from the reference point to the supporting device based on the equivalent thickness, and determine the first distance based on the third distance and the fourth distance. More descriptions of determining the first distance based on the third distance and the fourth distance may be found elsewhere in the present disclosure such as FIG. 9 and related descriptions.

In 740, size information of the scanning information may be determined based on the first distance and a medical image captured in the scan.

The medical image herein refers to a medical image obtained during a scanning process described in the operation 710. For example, when the scan is a historical scan mentioned in FIG. 3, the medical image may be the first medical image. When the scan is the current scan mentioned in FIG. 3, the medical image may be the second medical image.

In some embodiments, the processing device 120 may determine the size information of the scanning region based on the correction factor and the medical image. The correction factor may be configured to reflect a size of the object presented by each pixel in the medical image in a real world (rather than a size in the medical image). Specifically, the processing device 120 may calculate a product of the number of pixels belonging to the scanning region and the correction factor in the medical image as the size information of the scanning region.

In some embodiments, the processing device 120 may collect images of the reference object (e.g., a catheter, a ruler, or a steel ball with a known size (e.g., a size in the real world, abbreviated as a true size) through the medical imaging device 110, and determine the correction factor based on the true size of the reference object and the size of the reference object in the image. However, this process for determining the correction factor can only be performed when the true size of the reference object is known. In some embodiments, when an object (e.g., the scanning region) is placed at an isocenter of the medical imaging device 110, the processing device 120 may determine the correction factor based on the image of the object collected by the medical imaging device 110. In the medical imaging device 110, the radiation source and the detector may rotate around a common central point, a radiation axis of the radiation source may pass through a smallest sphere centered at the point, and a secondary common central point may be an isocenter point. However, this process for determining the correction factor requires the object to be placed at the isocenter point, otherwise, there may be a deviation in the determined correction factor, resulting in a deviation in the true size of the object determined based on the correction factor.

In some embodiments, the processing device 120 may determine the correction factor based on the first distance.

In some embodiments, the processing device 120 may obtain a second distance along the traveling direction of radiation rays between the radiation source and the detector, as well as reference size information of each detector unit of the detector, wherein the reference size information of the detector unit reflects a size of the detector unit. The second distance may be a distance in the real world rather than a distance in the image. Furthermore, the processing device 120 may determine the correction factor based on the first distance, the second distance, and the reference size information. Specifically, due to a similarity of triangles, the processing device 110 may calculate the correction factor based on the formulation $L1=h1*L/H$, wherein $L1$ represents the correction factor, $h1$ represents the first distance, $L$ represents the reference size information of each detector unit of the detector, and $H$ represents the second distance.

Through the process 700, size measurement of the scanning region can be easily and effectively achieved without the need for reference objects with known a dimension or limiting a position of a measuring object (e.g., the scanning region).

Figure 9:
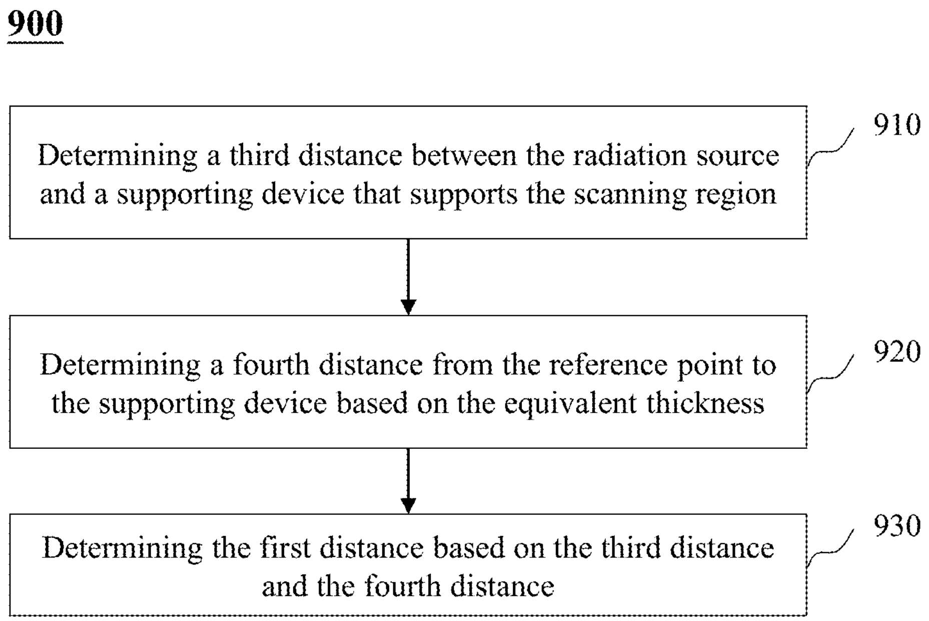
FIG. 9 is a flowchart illustrating an exemplary process for determining a first distance based on a third distance and a fourth distance according to some embodiments of the present disclosure.

FIG. 9 is a flowchart illustrating an exemplary process for determining a first distance based on a third distance and a fourth distance according to some embodiments of the present disclosure. As shown in FIG. 9, the process 900 may include the following operations.

In 910, a third distance between the radiation source and a supporting device that supports the scanning region may be determined.

The third distance may be a distance from the focal point of the radiation source along the traveling direction of radiation rays to the supporting device (e.g., a scanning bed). The third distance may be a distance in the real world rather than a distance in the image. In some embodiments, the third distance may be a distance from the focal point of the radiation source along the traveling direction of radiation rays to the reference point of the supporting device, wherein the reference point of the supporting device may be a point on the supporting device located in the traveling direction of radiation rays such as a point located in the traveling direction of radiation rays and at a top of the supporting device. As shown in FIG. 8A, the third distance may be a distance from the focal point 840 of the radiation source along the traveling direction of radiation rays 830 to the reference point 880 of the supporting device.

In some embodiments, the processing device 120 may obtain the third distance from the medical imaging device 110. Referring to the aforementioned embodiments, the position of the radiation source and the traveling direction of radiation rays may be the known information of the medical imaging device 110. The medical imaging device 110 may also obtain a position of the supporting device (e.g., through a positioning sensor installed on the supporting device). Therefore, the medical imaging device 110 may determine a third distance based on the position of the radiation source, the position of the supporting device, and the traveling direction of radiation rays.

In some embodiments, the processing device 120 may determine the third distance based on an optical image (e.g., the first optical image described in FIG. 7) of the medical imaging device 110 captured by the optical camera 150. For example, the processing device 110 may determine a connecting line between the focal point of the radiation source and the supporting device along the traveling direction of radiation rays in the optical image, and determine the third distance based on the number of pixels on the connecting line.

In some embodiments, the processing device 120 may establish the 3D model of the medical imaging device 110 based on the optical image captured by the optical camera 150, and further determine the third distance based on the 3D model of the medical imaging device 110.

In 920, a fourth distance from the reference point to the supporting device may be determined based on the equivalent thickness.

In some embodiments, the processing device 110 may designate a distance between the reference point of the scanning region and the reference point of the supporting device as the fourth distance. The fourth distance may be a distance in the real world rather than a distance in the image. As shown in FIG. 8A, the fourth distance may be a distance from the reference point 890 of the scanning region along the traveling direction of radiation rays 830 to the reference point 880 of the supporting device.

n some embodiments, the processing device 120 may determine the fourth distance from the reference point of the scanning region to the supporting device based on the equivalent thickness. For example, referring to FIG. 8A, when the traveling direction of radiation rays of the radiation source is a vertical direction and the reference point of the supporting device is located at the top of the supporting device, the fourth distance may be a half of the equivalent thickness.

In some embodiments, the processing device 120 may determine the fourth distance based on an optical image (e.g., the first optical image described in FIG. 7) collected by the optical camera 150 that includes the supporting device and the scanning region. For example, the processing device 120 may determine a connecting line between the reference point of the scanning region along the traveling direction of radiation rays and the reference point of the supporting device in the optical image, and determine the fourth distance based on the number of pixels on the connecting line.

In some embodiments, the processing device 120 may establish a 3D model of the supporting device based on the optical image captured by the optical camera 150, fuse the 3D model of the supporting device and the 3D model of the scanning region based on the spatial positional relationship, and determine the fourth distance based on the fused 3D model.

In 930, the first distance may be determined based on the third distance and the fourth distance.

In some embodiments, the processing device 110 may determine the first distance based on the third distance and the fourth distance. For example, referring to FIGS. 8A and 8B, when the supporting device is located between the radiation source and the scanning region, the first distance may be a sum of the third distance and the fourth distance. As another example, when the scanning region is located between the radiation source and the supporting device, the first distance may be a difference between the third distance and the fourth distance.

Figure 10:
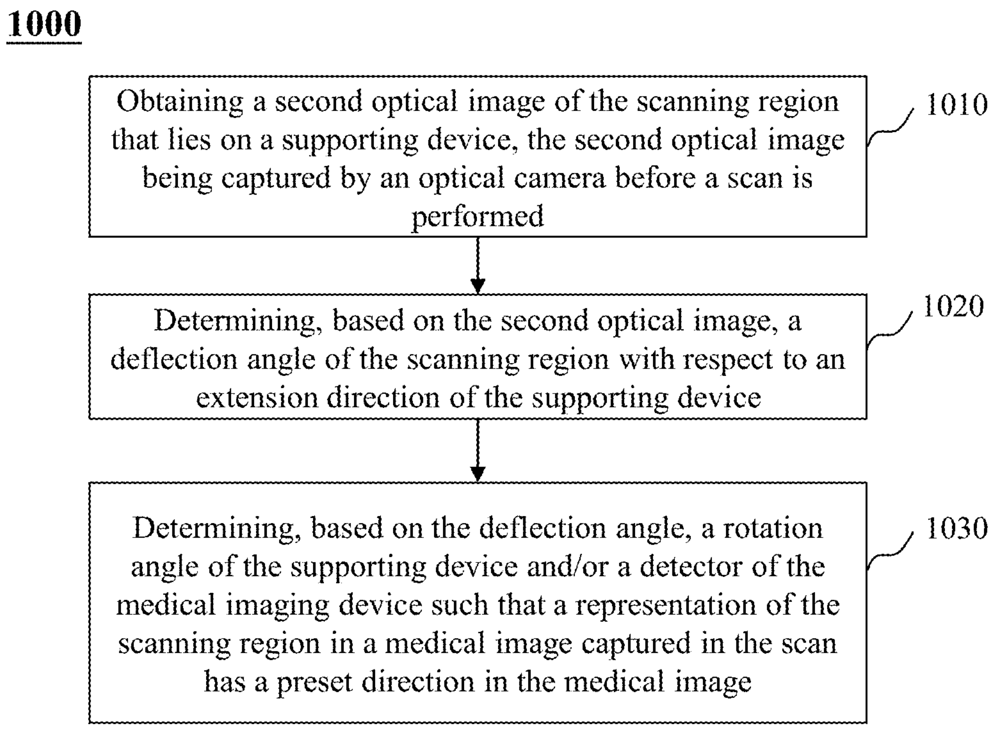
FIG. 10 is a flowchart illustrating an exemplary scan preparing process according to some embodiments of the present disclosure.

FIG. 10 is a flowchart illustrating an exemplary scan preparing process according to some embodiments of the present disclosure. In some embodiments, a process 1000 may be performed by the processing device 120 (e.g., the determination module 220). In some embodiments, the process 1000 may be performed before a scan to ensure that a representation of the scanning region in a resulting medical image of the scan has a preset direction in the medical image. As shown in FIG. 10, the process 1000 may include the following operations.

In 1010, a second optical image of the scanning region that is supported by a supporting device may be obtained, the second optical image may be captured by an optical camera before the scan is performed.

The scan herein refers to any scan, such as the historical scan or current scan described in FIG. 3.

In some embodiments, the second optical image may be a 2D image or a 3D image. In some embodiments, the second optical image may include a plurality of 2D images collected from different angles. In some embodiments, the second optical image may be a depth image.

In some embodiments, the processing device 120 may obtain at least two candidate optical images collected by at least two (e.g., three) optical cameras, and select one from the at least two candidate optical images. Furthermore, the processing device 120 may designate the selected candidate optical image as the second optical image. The processing device 120 may select the second optical image based on relevant information of the at least two candidate images (e.g., clarity, brightness, authenticity, etc.).

In some embodiments, by setting the at least two optical cameras, when some optical cameras are damaged, the second optical image may still be obtained through the undamaged optical camera to ensure a determination of the rotation angle.

In some embodiments, the second optical image may be the same optical image as the first optical image or a different optical image from the first optical image as described in connection with FIG. 7.

In 1020, a deflection angle of the scanning region with respect to an extension direction of the supporting device may be determined based on the second optical image.

The extension direction of the supporting device (e.g., the scanning bed) may also be referred to as a long axis direction of the supporting device.

Figure 11A:
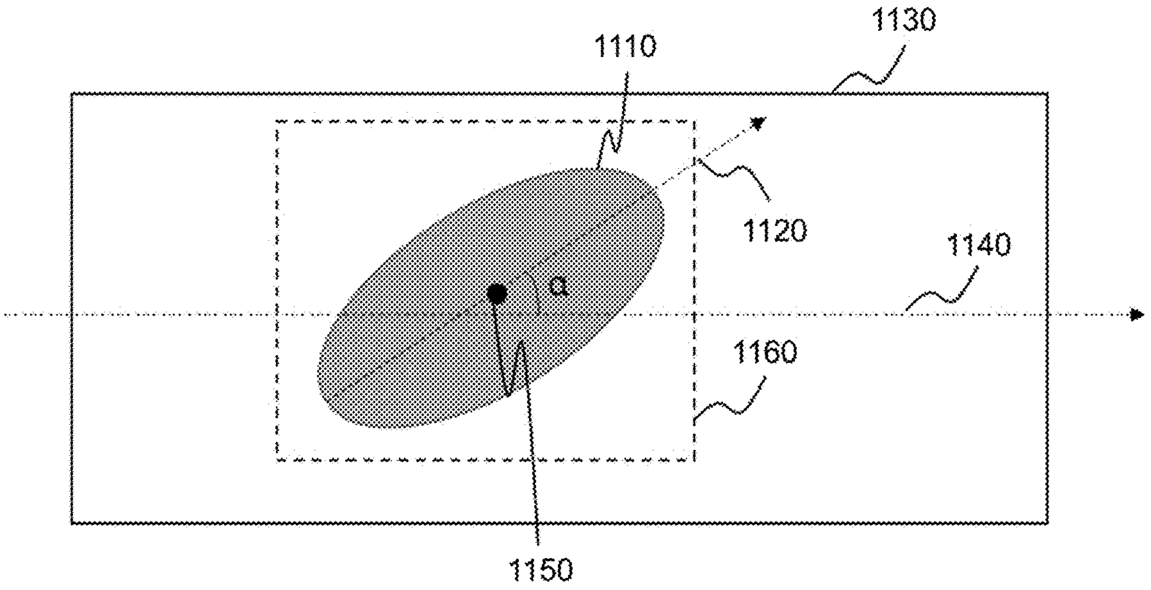
FIG. 11A is a schematic diagram illustrating an exemplary deflection angle according to some embodiments of the present disclosure.

Merely for example, referring to FIG. 11A, the processing device 120 may designate an angle α between a long axis direction 1120 of a scanning region 1110 and a long axis direction 1140 of a scanning bed 1130 as a deflection angle.

In some embodiments, the processing device 120 may establish a 3D model of the scanning object based on the second optical image. Furthermore, the processing device 120 may determine the angle between the long axis direction of the scanning region and the long axis direction of the supporting device based on the 3D of the scanning object. A plane where the long axis direction of the scanning region is located may be parallel or coincident with a plane where the long axis direction of the supporting device is located (e.g., a surface of the supporting device to support the scanning object). The optical camera 150 may be set above the supporting device to capture the second optical image including the scanning object and the supporting device at a top view angle.

In some embodiments, the second optical image may include a plurality of 2D images of the scanning object collected from different angles, and the processing device 120 may reconstruct a depth image of the scanning object based on the plurality of 2D images, and establish the 3D model of the scanning object based on the depth image of the scanning object. More descriptions of reconstructing the depth image may be found in above embodiments in the present disclosure.

In some embodiments, the second optical image may be a depth image, and the processing device 120 may directly establish the 3D model of the scanning object based on the depth image of the scanning object.

In some embodiments, the processing device 120 may determine the scanning region of the scanning object in the 3D model of the scanning object and determine a long axis direction of the scanning region. Furthermore, the processing device 120 may determine an angle between a long axis direction of the scanning region and a long axis direction of the supporting device.

In some embodiments, the processing device 120 may establish a fused 3D model based on an optical image of the scanning object (e.g., the patient) and the supporting device collected by the optical camera 150. The fused 3D model may be obtained by fusing the 3D model of the supporting device and the 3D model of the scanning object (or the scanning region) based on the spatial positional relationship. Furthermore, the processing device 120 may determine the long axis direction of the scanning region and the long axis direction of the supporting device based on the fused 3D model and determine the angle between the long axis direction of the scanning region and the long axis direction of the supporting device.

In some embodiments, the processing device 120 may determine the deflection angle of the scanning region by processing the second optical image using an angle prediction model, wherein the angle prediction model may be a trained machine learning model. The processing device 120 may train an initial model based on a plurality of training samples and corresponding training labels to obtain the angle prediction model. Each training sample may include an optical image of a sample scanning region and a sample supporting device, and the training label may be a deflection angle label of the sample scanning region relative to a long axis direction of the sample supporting device. In some embodiments, the deflection angle label may be manually calibrated.

In some embodiments, the processing device 120 may identify at least two feature points of the scanning region from the second optical image; and determine the deflection angle based on the at least two feature points. For example, the processing device 120 may determine the long axis direction of the scanning region based on a spatial relationship between the long axis direction of the scanning region and the at least two feature points of the scanning region (e.g., the long axis direction passes through the at least two feature points). Furthermore, the processing device 120 may determine the deflection angle based on the long axis direction of the scanning region and the long axis direction of the supporting device. More descriptions of the feature points may refer to the above embodiments.

In 1030, a rotation angle of the supporting device and/or a detector of the medical imaging device may be determined based on the deflection angle such that a representation of the scanning region in a medical image captured in the scan has a preset direction in the medical image.

The medical image here refers to a medical image obtained in the scan as described in operation 1010, such as the first medical image obtained in the historical scan or the current scan.

Figure 11B:
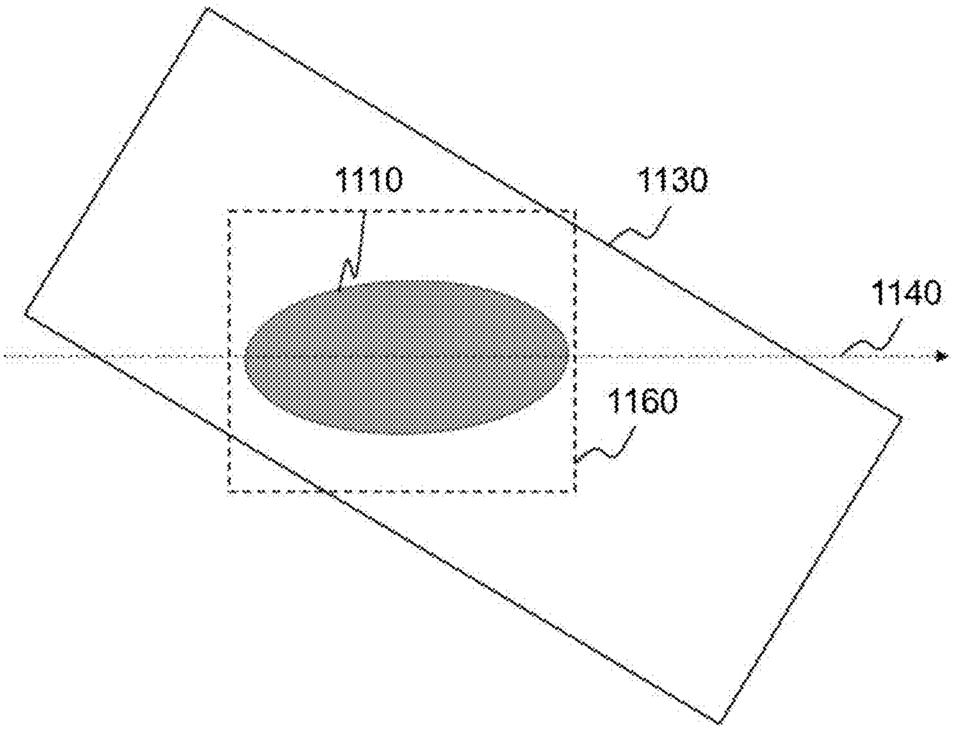
FIG. 11B is a schematic diagram illustrating an exemplary supporting device after rotating based on a deflection angle according to some embodiments of the present disclosure.

In some embodiments, the processing device 120 may control a rotation of the supporting device and/or the detector based on the rotation angle to present the scanning region in a predetermined direction (also known as a forward display) in the medical image obtained during the scan. In some embodiments, when the long axis direction of the scanning region in the medical image is parallel to a boundary of the medical image, the scanning region may be considered as being displayed in a forward direction in the medical image. Taking FIG. 11A as an example, in response to determining that a deflection angle 1120 a between a long axis direction of a scanning region 1110 and a long axis direction of a scanning bed 1130 is greater than a preset threshold, the processing device 120 may control the scanning bed 1130 to rotate a certain angle along a clockwise direction with a center 1150 of the scanning region 1110 as a rotation center point to reduce the deflection angle $\alpha$, and a rotation angle of the scanning bed 1130 may be equal to the deflection angle $\alpha$ before the rotation. As shown in FIG. 11B, a long axis direction 1120 of the rotated scanning region 1110 may be parallel to a long axis direction 1140 of an imaging plane 1160 of the detector, such that a representation of the scanning region 1110 has a forward direction in the medical image.

Figure 11C:
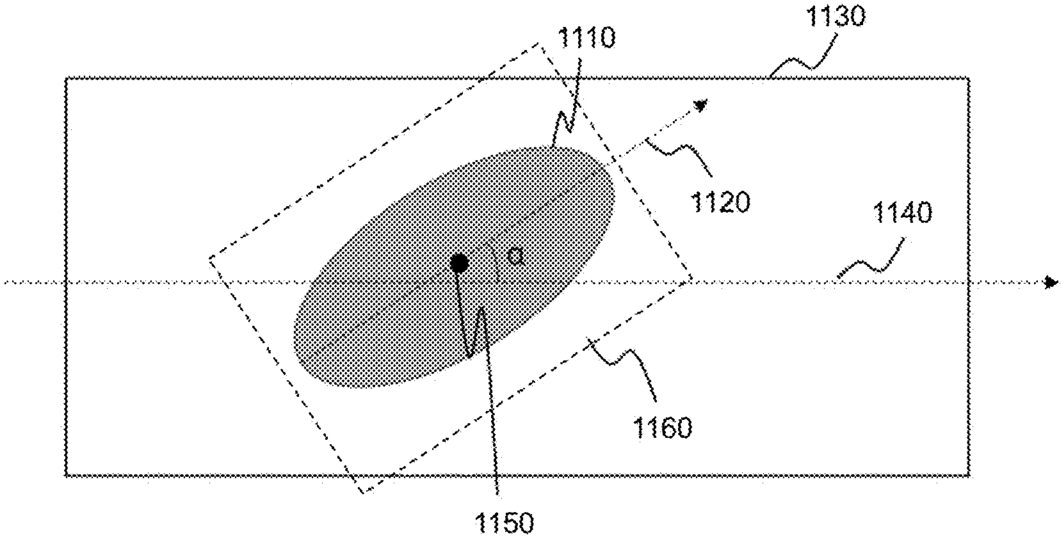
FIG. 11C is a schematic diagram illustrating an exemplary detector after rotating based on a deflection angle according to some embodiments of the present disclosure.
Figure 11D:
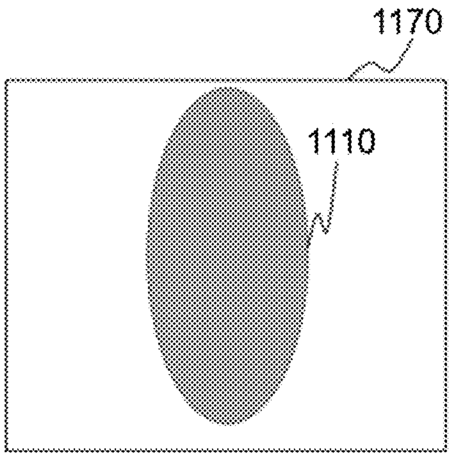
FIG. 11D is a schematic diagram illustrating an exemplary medical image obtained after a supporting device or a detector is rotated based on a deflection angle according to some embodiments of the present disclosure.

In some embodiments, the processing device 120 may control a rotation of the detector based on the deflection angle before performing the scan. Taking FIG. 11A as an example, the processing device 120 may rotate the detector by a certain angle in a counterclockwise direction to reduce the deflection angle of the long axis direction of the scanning region compared to the long axis direction of the supporting device. The rotation angle of the detector may be equal to the deflection angle $\alpha$ before the rotation. As shown in FIG. 11C, the long axis direction of the imaging plane 1160 of the rotated detector may be parallel to the long axis direction 1120 of the scanning region 1110. As shown in FIG. 11D, the processing device 120 may control the detector to rotate at a certain angle before turning on the scan, such that a representation of the scanning region 1110 has a forward direction in a medical image 1170. As shown in FIG. 11C, the long axis direction of the imaging plane 1160 of the rotated detector may be parallel to the long axis direction 1120 of the scanning region 1110. As shown in FIG. 11D, the processing device 120 may control the detector to rotate at a certain angle before performing the scan, such that a representation of the scanning region 1110 has a forward direction in the medical image 1170.

By performing the process 1000, the detector and/or the supporting device can automatically rotate to maintain the forward display of the scanning region in the medical image. The automatic rotation of the detector and/or the supporting device can avoid additional operations and exposure to radiation for workers. In addition, by directly rotating the detector and/or the supporting device instead of rotating a medical image, aa complete medical image can be collected and the problem of incomplete images caused by image rotation can be avoided.

Figure 12A:
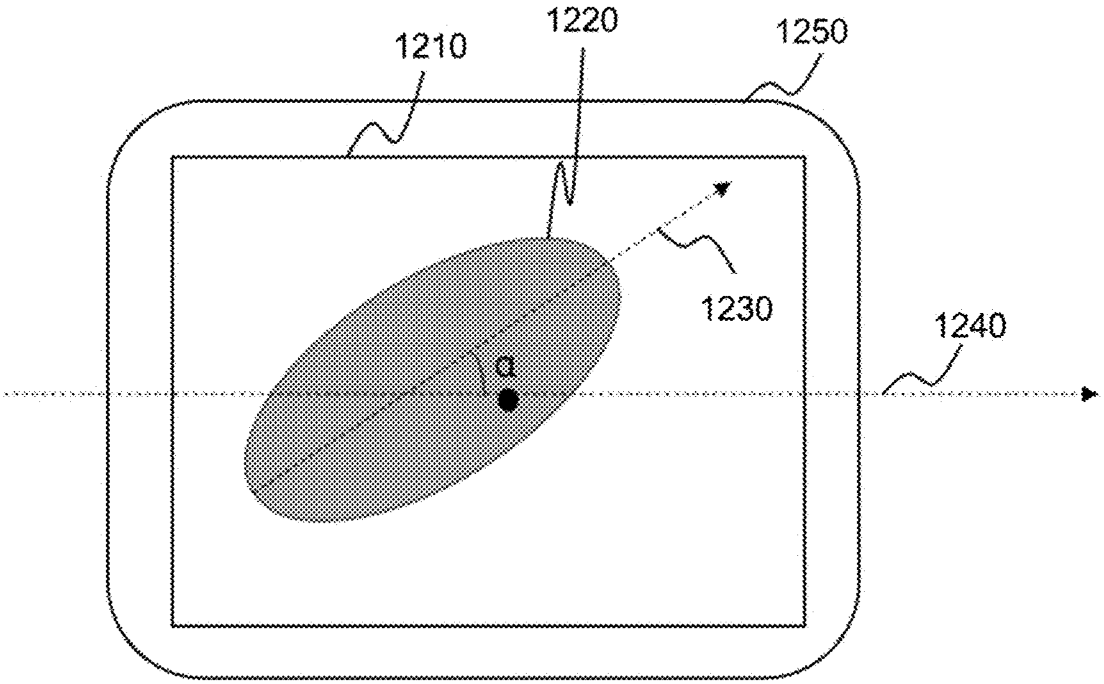
FIG. 12A is a schematic diagram illustrating an exemplary medical image before a supporting device or a detector is rotated according to some embodiments of the present disclosure.
Figure 12B:
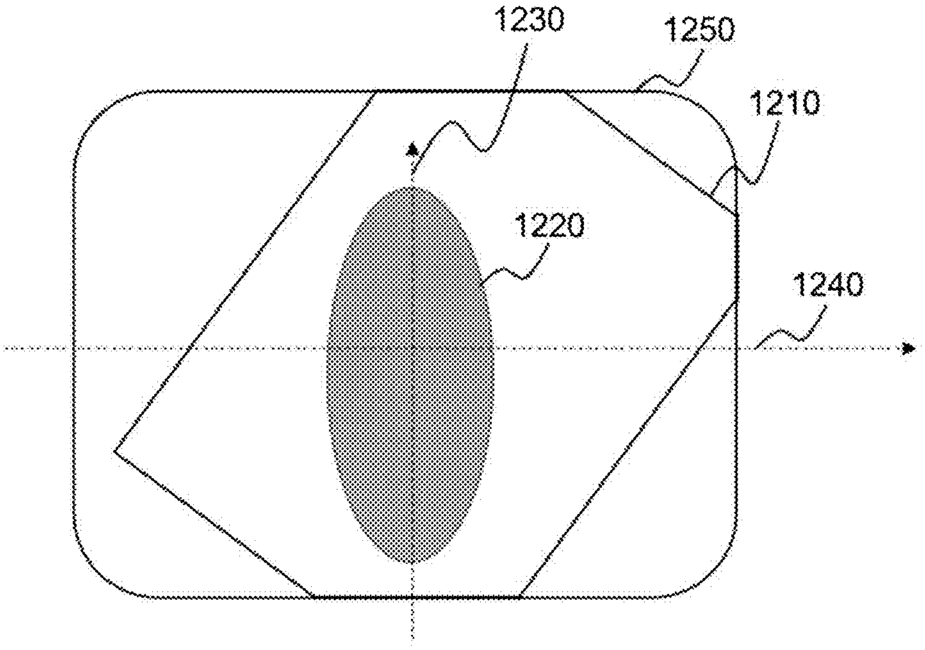
FIG. 12B is a schematic diagram illustrating an exemplary medical image after a supporting device or a detector is rotated according to some embodiments of the present disclosure.

In some embodiments, the processing device 120 may determine the rotation angle of the medical image based on the deflection angle and rotate the medical image according to the rotation angle. For example, as shown in FIG. 12A, in the medical image 1210 displayed on a screen 1250 before correction, there is an angle $\alpha$ in the long axis direction 1230 of the scanning region 1220 of the scanning object compared to a horizontal direction 1240. The representation of the scanning region 1220 of the scanning object does not have a forward direction, and the processing device 120 may rotate the medical image 1210 in a counterclockwise direction at a certain angle around a center of the medical image 1210, such that the representation of scanning region 1220 in the medical image 1210 has a forward direction. A size of the rotation angle of the medical image 1210 may be ($90°-\alpha$). As shown in FIG. 12B, in the rotated medical image 1210 displayed on the screen 1250, the long axis direction of the scanning region 1220 may be perpendicular to the horizontal direction 1240, and the representation of the scanning region 1220 has a forward direction in the medical image 1210.

In some embodiments, when the deflection angle meets a preset threshold, the processing device 120 may rotate the detector of the supporting device and/or medical imaging device 110 or rotate the medical image, such that the representation of the scanning region has a forward direction in the medical image. The preset threshold represents a maximum value of the deflection angle that does not require correction. In some embodiments, the processing device 120 may obtain the preset threshold from the medical imaging device 110, the user terminal 130, the storage device 140, and/or external data sources.

By directly rotating the image, the imaging time can be reduced and the user experience is improved. However, as shown in FIG. 12B, the image rotation may cause edges of the original medical image to be cropped.

In some embodiments, after the display correction regarding the current scanning region is completed, the processing device 120 may control the supporting device to move to scan a next scanning region and continue with display correction regarding the next scanning region. Through the continuous display correction, representations of different scanning regions both have a forward direction in the corresponding medical images.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for medical imaging, comprising:

at least one storage medium including a set of instructions; and at least one processor in communication with the at least one storage medium, wherein when executing the set of instructions, the at least one processor is directed to cause the system to perform operations including:

obtaining historical state information of a scanning region in a historical scan and current state information of the scanning region in a current scan to be performed;

determining whether historical parameter values of one or more imaging parameters used in the historical scan need to be updated based on a comparison result between the historical state information and the current state information;

in response to determining that the historical parameter values of the one or more imaging parameters used in the historical scan need to be updated, determining first feature information of a first medical image captured in the historical scan;

determining the updated parameter values of the one or more imaging parameters based on the historical state information and the current state information such that a similarity degree between the first feature information and second feature information of a second medical image captured in the current scan is within a preset range, the first feature information and the second feature information relating to at least one of a radiation incidence center, a radiation incidence angle, or an image feature parameter that affects visual presentation of the first medical image and the second medical image, wherein the updated parameter values of the one or more imaging parameters are determined according to a process including one or more iterations, and each of the one or more iterations includes:

determining a predicted second medical image based on the current state information, the first medical image, and initial parameter values of the one or more imaging parameters using an image prediction model, the image prediction model being a trained machine learning model;

determining whether a similarity degree between the first feature information and third feature information of the predicted second medical image is within the preset range;

in response to determining that the similarity degree between the first feature information and the third feature information is out of the preset range, determining adjusted parameter values of the one or more imaging parameters based on the first feature information and the third feature information, and designating the adjusted parameter values as initial parameter values in a next iteration; or in response to determining that the similarity degree between the first feature information and the third feature information is within the preset range, designating the initial parameter values of the one or more imaging parameters as the updated parameter values of the one or more imaging parameters; and directing a medical imaging device to perform the current scan based on the updated parameter values of the one or more imaging parameters.

2. The system of claim 1, the historical state information and the current state information relate to at least one of:

whether the scanning region is fixed by a fixing device, whether a distance between the scanning region and a radiation source of the medical imaging device is within a preset distance range, whether the scanning region has a preset posture, or whether a radiation ray filtering device is placed between the scanning region and the medical imaging device.

3. The system of claim 1, wherein the one or more imaging parameters include at least one of:

a position parameter of one or more movable components of the medical imaging device, an exposure parameter, or an image post-processing parameter.

4. The system of claim 1, wherein the determining updated parameter values of the one or more imaging parameters based on the historical state information and the current state information comprises:

for each of at least part of the one or more imaging parameters, determining, based on a first medical image captured in the historical scan, a reference range of the imaging parameter;

determining, based on the current state information and the historical state information, a candidate parameter value of the imaging parameter; and determining, based on the candidate parameter value, the updated parameter value of the imaging parameter that is within the reference range of the imaging parameter.

5. The system of claim 1, wherein the determining updated parameter values of the one or more imaging parameters based on the historical state information and the current state information comprises:

determining the updated parameter values by processing the historical state information, the current state information, and the historical parameter values using a parameter prediction model, the parameter prediction model being a trained machine learning model.

6. The system of claim 1, wherein the operations further include:

determining size information of the scanning region based on a medical image captured in the historical scan or the current scan by:

obtaining a first optical image of the scanning region captured by an optical camera in the historical scan or the current scan;

determining, based on the first optical image, an equivalent thickness of the scanning region along a traveling direction of radiation rays in the historical scan or the current scan;

determining, based on the equivalent thickness, a first distance between a radiation source and a reference point of the scanning region; and determining, based on the first distance and the medical image, the size information of the scanning region.

7. The system of claim 6, wherein the determining, based on the first distance and the medical image, the size information of the scanning region comprises:

obtaining a second distance between the radiation source and a detector along the traveling direction and reference size information of each detector unit of the detector;

determining a correction coefficient based on the first distance, the second distance, and the reference size information;

determining the size information based on the correction coefficient and the medical image.

8. The system of claim 6, wherein the determining, based on the equivalent thickness, a first distance between a radiation source and a reference point of the scanning region comprises:

determining a third distance between the radiation source and a supporting device that supports the scanning region;

determining a fourth distance from the reference point to the supporting device based on the equivalent thickness; and determining the first distance based on the third distance and the fourth distance.

9. The system of claim 1, wherein the operations further include:

obtaining a second optical image of the scanning region that is supported by a supporting device, the second optical image being captured by an optical camera before the current scan is performed;

determining, based on the second optical image, a deflection angle of the scanning region with respect to an extension direction of the supporting device;

determining, based on the deflection angle, a rotation angle of the supporting device and/or a detector of the medical imaging device such that a representation of the scanning region in a second medical image captured in the current scan has a preset direction in the second medical image.

10. The system of claim 9, wherein the deflection angle of the scanning region is determined by processing the second optical image using an angle prediction model, the angle prediction model being a trained machine learning model.

11. The system of claim 9, wherein the determining a deflection angle of the scanning region with respect to an extension direction of the supporting device comprises:

identifying at least two feature points of the scanning region from the second optical image; and determining the deflection angle based on the at least two feature points.

12. The system of claim 1, wherein the historical state information and the current state information relate to at least one of:

whether the scanning region is fixed by a fixing device, wherein the fixing device includes at least one of a plaster cast, a neck bracket, an elbow joint fixation bracket, a knee joint fixation bracket, or an ankle fixation bracket, whether a distance between the scanning region and a radiation source of the medical imaging device is within a preset distance range, or whether a radiation ray filtering device is placed between the scanning region and the medical imaging device.

13. The system of claim 4, wherein the determining, based on a first medical image captured in the historical scan, a reference range of the imaging parameter includes:

determining the reference range of the imaging parameter based on one or more image feature parameters of the first medical image, the one or more image feature parameters referring to parameters that affect a visual presentation of the first medical image.

14. A system, comprising:

at least one storage medium including a set of instructions; and at least one processor in communication with the at least one storage medium, wherein when executing the set of instructions, the at least one processor is directed to cause the system to perform operations including:

obtaining an optical image of a scanning region captured by an optical camera in a scan;

determining, based on the optical image, an equivalent thickness of the scanning region along a traveling direction of radiation rays in the scan;

determining, based on the equivalent thickness, a first distance between a radiation source and a reference point of the scanning region; and determining, based on the first distance and a medical image captured in the scan, size information of the scanning region.

15. The system of claim 14, wherein the determining, based on the first distance and a medical image captured in the scan, size information of the scanning region comprises:

obtaining a second distance between the radiation source and a detector along the traveling direction and reference size information of each detector unit of the detector;

determining a correction coefficient based on the first distance, the second distance, and the reference size information;

determining the size information based on the correction coefficient and the medical image.

16. The system of claim 14, wherein the determining, based on the optical image, an equivalent thickness of the scanning region along a traveling direction of radiation rays in the scan comprises:

determining a third distance between the radiation source and a supporting device that supports the scanning region;

determining a fourth distance from the reference point to the supporting device based on the equivalent thickness; and determining the first distance based on the third distance and the fourth distance.

17. A system, comprising:

at least one storage medium including a set of instructions; and at least one processor in communication with the at least one storage medium, wherein when executing the set of instructions, the at least one processor is directed to cause the system to perform operations including:

obtaining an optical image of a scanning region that is supported by a supporting device, the optical image being captured by an optical camera before a scan is performed;

determining, based on the optical image, a deflection angle of the scanning region with respect to an extension direction of the supporting device;

determining, based on the deflection angle, a rotation angle of the supporting device and/or a detector of a medical imaging device for performing the scan such that a representation of the scanning region in a medical image captured in the scan has a preset direction in the medical image.

18. The system of claim 17, wherein the deflection angle of the scanning region is determined by processing the optical image using an angle prediction model, the angle prediction model being a trained machine learning model.

19. The system of claim 17, wherein the determining, based on the optical image, a deflection angle of the scanning region with respect to an extension direction of the supporting device comprises:

identifying at least two feature points of the scanning region from the optical image; and determining the deflection angle based on the at least two feature points.

* * * * *